(12) United States Patent
Majors et al.

(10) Patent No.: US 12,201,331 B2
(45) Date of Patent: Jan. 21, 2025

(54) IMPLANTS, SYSTEMS, AND METHODS OF USE

(71) Applicant: Paragon 28, Inc., Englewood, CO (US)

(72) Inventors: Benjamin Majors, Englewood, CO (US); Thomas R. Williams, Bon Aqua, TN (US); Peter Andrew Mladinich, Parker, CO (US); Kenneth Allan Roggow, Denver, CO (US)

(73) Assignee: Paragon 28, Inc., Englewood, CO (US)

( * ) Notice: Subject to any disclaimer, the term of this patent is extended or adjusted under 35 U.S.C. 154(b) by 555 days.

(21) Appl. No.: 17/446,335

(22) Filed: Aug. 30, 2021

(65) Prior Publication Data

US 2021/0386463 A1  Dec. 16, 2021

Related U.S. Application Data

(63) Continuation of application No. PCT/US2020/020445, filed on Feb. 28, 2020.

(60) Provisional application No. 62/812,247, filed on Feb. 28, 2019.

(51) Int. Cl.
  *A61B 17/72* (2006.01)
(52) U.S. Cl.
  CPC ...... *A61B 17/7291* (2013.01); *A61B 17/7225* (2013.01); *A61B 17/7241* (2013.01)
(58) Field of Classification Search
  CPC .............. A61B 17/72; A61B 17/7208; A61B 17/7216; A61B 17/7225; A61B 17/7233; A61B 17/7241; A61B 17/7283; A61B 17/7291; A61F 2002/0823; A61F 2002/0829; A61F 2002/0835; A61F 2002/0841
  See application file for complete search history.

(56) References Cited

U.S. PATENT DOCUMENTS

| | | |
|---|---|---|
| 8,491,583 B2 | 7/2013 | Gall |
| 9,445,850 B2 | 9/2016 | Kinmon |
| 10,034,742 B2 | 7/2018 | Diduch et al. |
| 10,076,374 B2 | 9/2018 | Diduch et al. |
| 2009/0099571 A1 | 4/2009 | Cresina |
| 2009/0149861 A1 | 6/2009 | Brodsky |
| 2011/0245885 A1 | 10/2011 | Powell |
| 2012/0109217 A1 | 5/2012 | Perineau |
| 2013/0046311 A1 | 2/2013 | Blake |

(Continued)

FOREIGN PATENT DOCUMENTS

WO  2015164689  10/2015

OTHER PUBLICATIONS

Extended European Search Report for European Application No. 20762486.7, Nov. 25, 2022, 7 pages.

(Continued)

*Primary Examiner* — Ellen C Hammond
(74) *Attorney, Agent, or Firm* — Heslin Rothenberg Farley & Mesiti P.C.; Jacquelyn A. Graff, Esq.

(57) ABSTRACT

Implants, systems and methods for correcting bone deformities and fractures in the lower extremity are disclosed. Specifically, implants, systems and methods used for correcting bone deformities and/or fractures in the foot using compression are disclosed. A nail system including a first member with a first deformable member positioned at a first end of the first member and a second member received within the first member.

25 Claims, 36 Drawing Sheets

(56) References Cited

U.S. PATENT DOCUMENTS

| | | |
|---|---|---|
| 2013/0085502 A1 | 4/2013 | Harrold |
| 2013/0116693 A1 | 5/2013 | Nelson |
| 2014/0114312 A1 | 4/2014 | Krause |
| 2014/0214101 A1 | 7/2014 | Roethlisberger et al. |
| 2015/0057663 A1 | 2/2015 | Kinmon |
| 2015/0305791 A1 | 10/2015 | Purohit |
| 2017/0189085 A1* | 7/2017 | Krause ............... A61B 17/7208 |
| 2017/0290656 A1 | 10/2017 | Piccirillo et al. |
| 2017/0296241 A1 | 10/2017 | Garlock et al. |
| 2018/0263669 A1 | 9/2018 | Peterson et al. |

OTHER PUBLICATIONS

International Preliminary Report on Patentability for International Application No. PCT/US2020/049007 dated Mar. 15, 2022, 8 pages, International Bureau of WIPO.

Didomenico et al., "Intramedullary Nail Fixation for Tibiotalocalcaneal Arthrodesis", International Advances in Foot and Ankle Surgery. Springer, London, pp. 453-465, 2012.

International Search Report and Written Opinion of the International Searching Authority for PCT/US2020/020445, May 6, 2020, 10 pages.

\* cited by examiner

IMPLANTS, SYSTEMS, AND METHODS OF USE

CROSS REFERENCE TO RELATED APPLICATION

This application is a continuation of PCT/US2020/020445 filed Feb. 28, 2020 and entitled Implants, Systems, and Methods of Use, which claims priority benefit under 35 U.S.C. § 119(e) of U.S. provisional application No. 62/812,247 filed Feb. 28, 2019, entitled Implants, Systems and Methods of Use, which is incorporated herein by reference in its entirety.

FIELD OF THE INVENTION

The present invention relates generally to general surgery, podiatric, and orthopaedic implants used for correcting bone deformities. More specifically, but not exclusively, the present invention relates to implants, systems and methods for correcting bone deformities.

BACKGROUND OF THE INVENTION

Commonly, a fusion of the tibia-talus-calcaneus (TTC) complex is required due to pathology, trauma or failed previous operations. The currently available options for fusing the three bones together include intramedullary nails (IM), crossing screws or plating. The currently available implants cross two joints: the tibio-talar or ankle joint and the talo-calcaneal or subtalar joint. During the use of the currently available implants there is a period of resorption that occurs causing a gaping between joint surfaces. This gaping can lead to a failed fusion (nonunion) and ultimately device failure. Thus, new implants, systems and methods of use are needed to ensure that gaping is prevented or minimized and bony opposition is maintained during the healing process.

SUMMARY OF THE INVENTION

Aspects of the present invention provide implants, systems and methods for correcting bone deformities in the foot and ankle.

In one aspect, provided herein is a nail system. The nail system includes a first member with a first deformable member positioned at a first end of the first member and a second member coupled to the first member.

In another aspect, provided herein is a method of using the nail systems. The method including inserting at least one nail system into a patient and releasing the nail system to provide compression on the patient's joint.

These, and other objects, features and advantages of this invention will become apparent from the following detailed description of the various aspects of the invention taken in conjunction with the accompanying drawings.

BRIEF DESCRIPTION OF DRAWINGS

The accompanying drawings, which are incorporated in and constitute a part of the specification, illustrate embodiments of the invention and together with the detailed description herein, serve to explain the principles of the invention. The drawings are only for purposes of illustrating preferred embodiments and are not to be construed as limiting the invention. It is emphasized that, in accordance with the standard practice in the industry, various features are not drawn to scale. In fact, the dimensions of the various features may be arbitrarily increased or reduced for clarity of discussion. The foregoing and other objects, features and advantages of the invention are apparent from the following detailed description taken in conjunction with the accompanying drawings in which.

DETAILED DESCRIPTION FOR CARRYING OUT THE INVENTION

Figure 1:
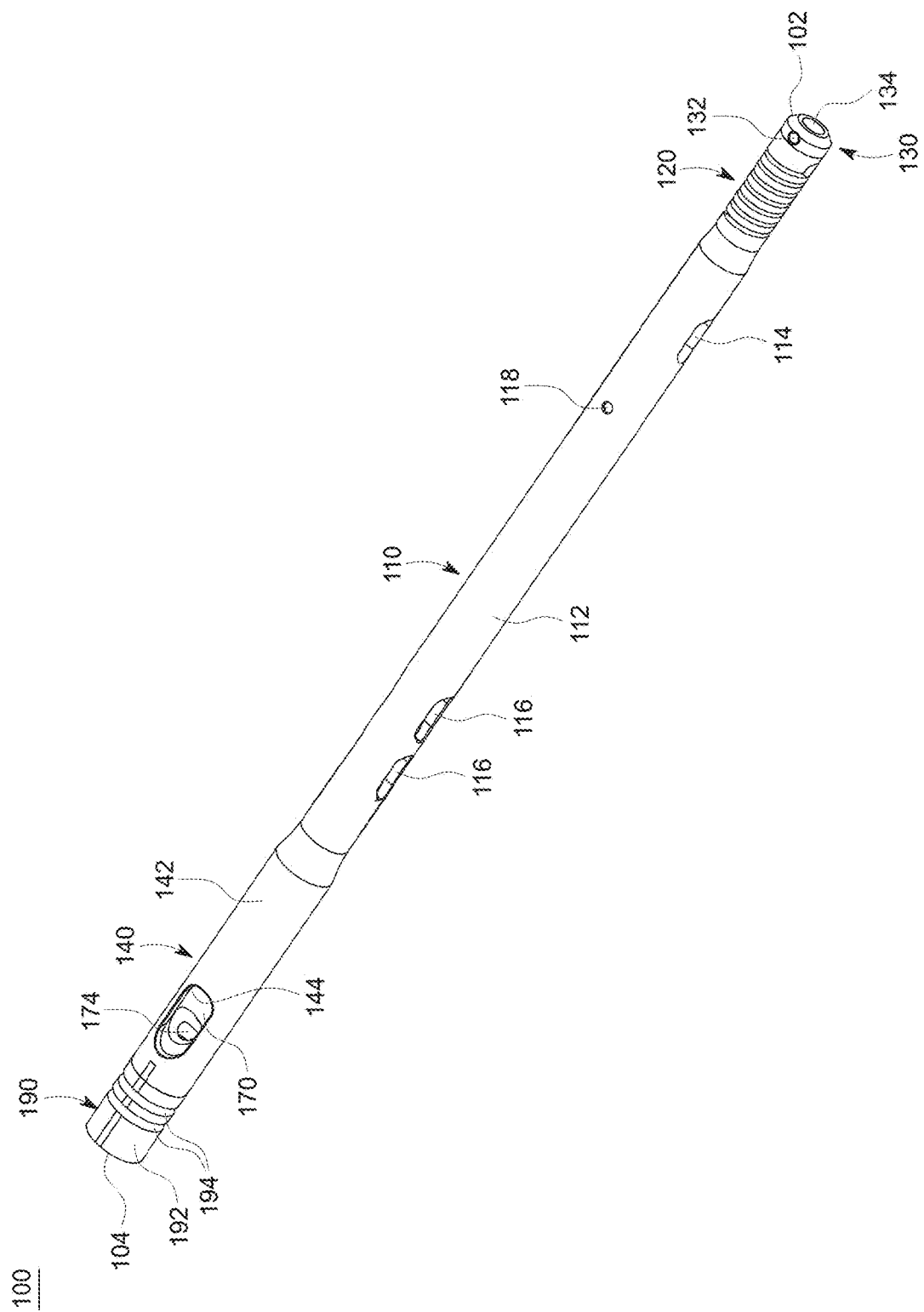
FIG. 1 is a first perspective view of a dynamic nail, in accordance with an aspect of the present disclosure.
Figure 2:
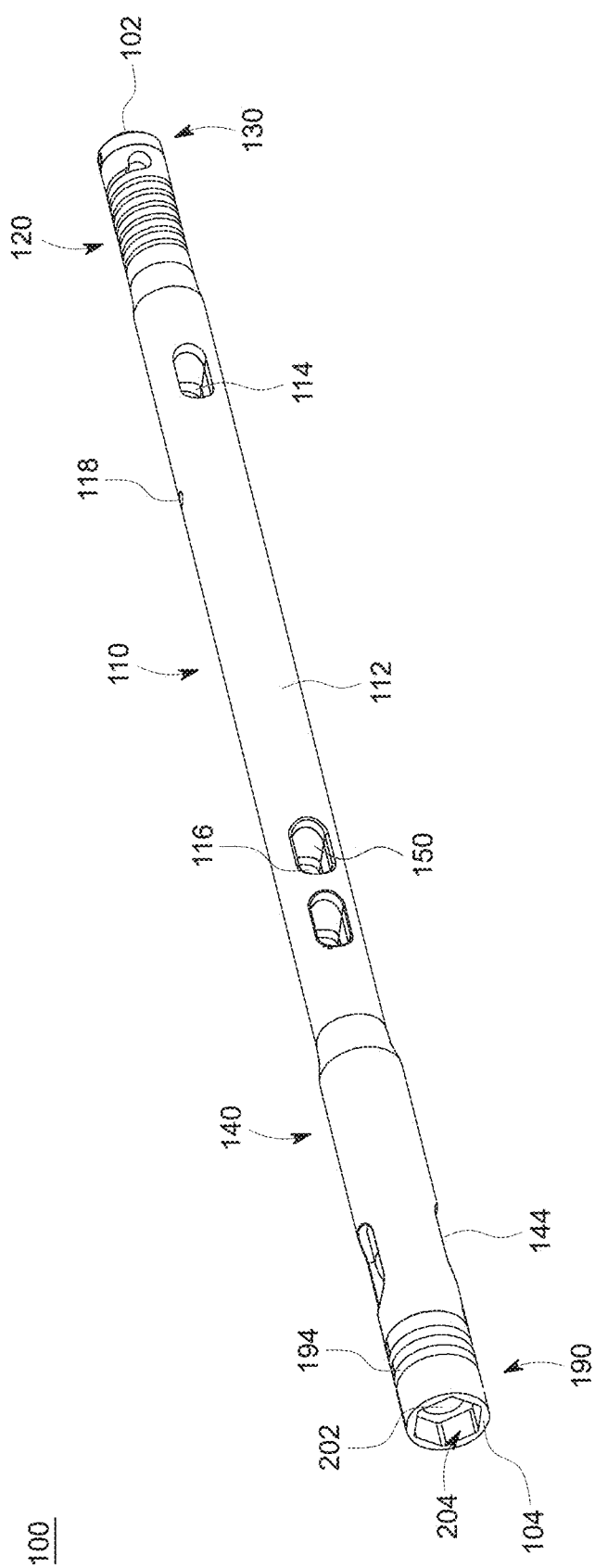
FIG. 2 is a second perspective view of the dynamic nail of FIG. 1, in accordance with an aspect of the present disclosure.

Generally stated, disclosed herein are implants and systems for correcting bone deformities. Further, methods for correcting bone deformities using the implants and systems are discussed.

In this detailed description and the following claims, the words proximal, distal, anterior or plantar, posterior or dorsal, medial, lateral, superior and inferior are defined by their standard usage for indicating a particular part or portion of a bone or implant according to the relative disposition of the natural bone or directional terms of reference. For example, "proximal" means the portion of a device or implant nearest the torso, while "distal" indicates the portion of the device or implant farthest from the torso. As for directional terms, "anterior" is a direction towards the front side of the body, "posterior" means a direction towards the back side of the body, "medial" means towards the midline of the body, "lateral" is a direction towards the sides or away from the midline of the body, "superior" means a direction above and "inferior" means a direction below another object or structure. Further, specifically in regards to the foot, the term "dorsal" refers to the top of the foot and the term "plantar" refers the bottom of the foot.

Similarly, positions or directions may be used herein with reference to anatomical structures or surfaces. For example, as the current devices, systems, instrumentation and methods are described herein with reference to use with the bones of the ankle, the bones of the foot, ankle and lower leg may be used to describe the surfaces, positions, directions or orientations of the devices, systems, instrumentation and methods. Further, the devices, systems, instrumentation and methods, and the aspects, components, features and the like thereof, disclosed herein are described with respect to one side of the body for brevity purposes. However, as the human body is relatively symmetrical or mirrored about a line of symmetry (midline), it is hereby expressly contemplated that the devices, systems, instrumentation and methods, and the aspects, components, features and the like thereof, described and/or illustrated herein may be changed, varied, modified, reconfigured or otherwise altered for use or association with another side of the body for a same or similar purpose without departing from the spirit and scope of the disclosure. For example, the devices, systems, instrumentation and methods, and the aspects, components, features and the like thereof, described herein with respect to the right leg may be mirrored so that they likewise function with the left leg. Further, the devices, systems, instrumentation and methods, and the aspects, components, features and the like thereof, disclosed herein are described with respect to the leg for brevity purposes, but it should be understood that the devices, systems, instrumentation and methods may be used with other bones of the body having similar structures.

Referring now to FIGS. 1-14, an implant 100 is shown. The implant 100 is an IM nail or crossing screw. The implant 100 includes a first member or outer sheath 110, a second member or inner rod 150, a coupling member 130 to secure the first member 110 to the second member 150 at the first or proximal end 102, and a tension screw 190 to secure the first member 110 to the second member 150 at the second or distal end 104.

With continued reference to FIGS. 1-14, the first member 110 includes a body portion or shaft 112, a deformable member 120 coupled to a first end of the body portion 112, and a distal end portion 140 coupled to a second end of the body portion 112. The first member 110 also includes a first or proximal through hole or fastener hole 114 positioned near the deformable member 120 and at least one second through hole or fastener hole 116 positioned near the distal end portion 140. The holes 114, 116 may be, for example, elongated or oval holes. The holes 114, 116 may extend through the body portion 112 from one side to the other perpendicular to the longitudinal axis of the first member 110. The holes 114, 116 may be, for example, sized and shaped or configured to receive a bone screw or bone fastener. The body portion 112 may also include at least one anti-rotation pin opening 118 extending through the body portion 112 from one side to the other side. The pin opening 118 is, for example, sized and shaped or configured to receive an anti-rotation pin 106. The first member 110 may also include a through hole 122 extending through the first member 110 along the longitudinal axis of the first member 110.

As shown in FIGS. 1-8 and 11-14, the deformable member, spring or proximal external spring member 120 is coupled to the first end of the body portion 112. When inserted into a patient, the proximal external spring 120 resides inside the tibia anatomically. The spring 120 may be inserted, for example, in a first compressed position and once implantation is complete, the spring 120 may move to at least one second partially compressed position. As shown, the deformable member 120 is a helical cut, machined spring. The helical spring 120 is cut into, one piece, or integral with the outer sheath 110 of the nail 100. The spring 120 may be compressed to provide stored energy required to apply a compressive force to the tibio-talar joint by "pulling" the talus toward the tibia once implanted.

Figure 14:
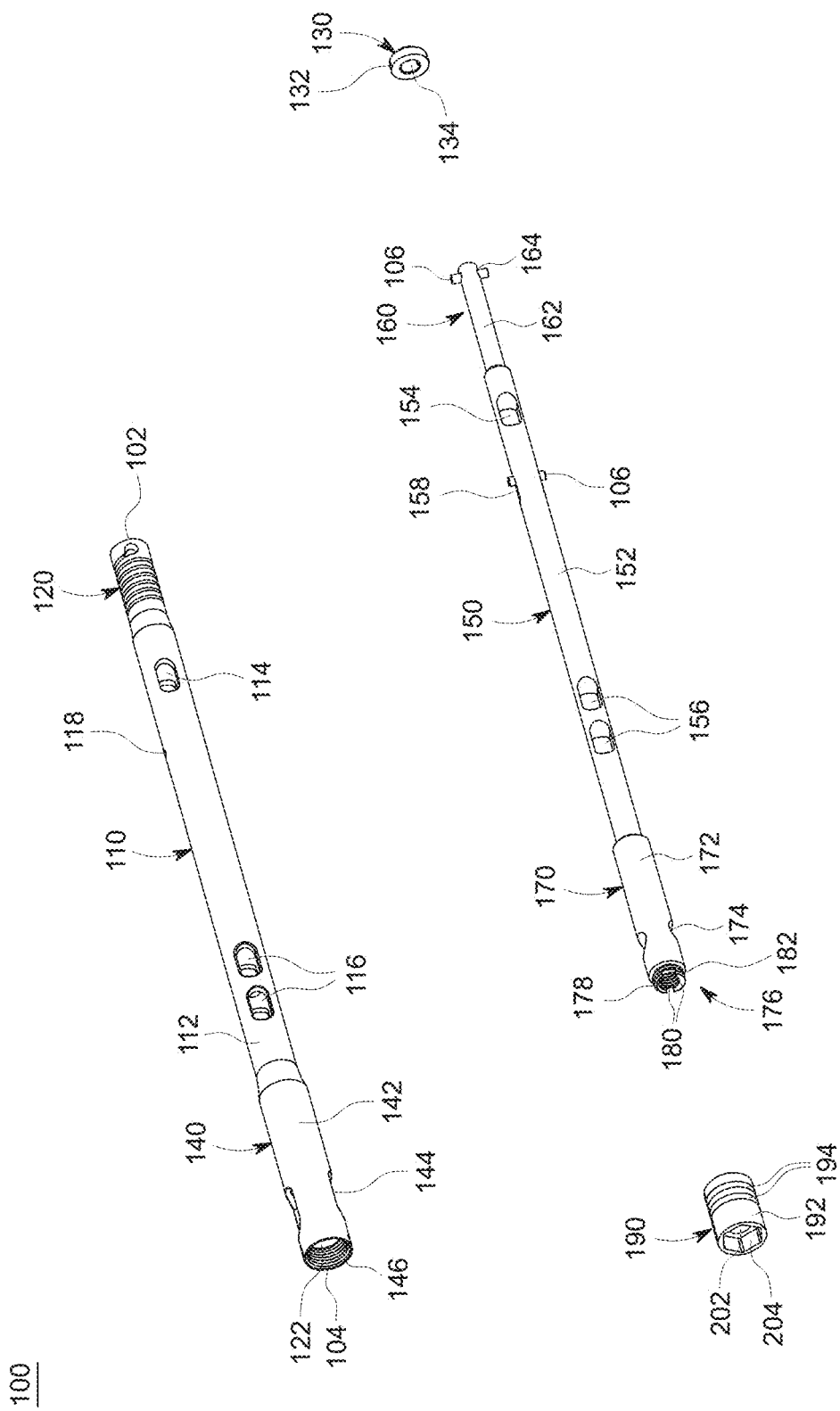
FIG. 14 is an exploded, second perspective view of the dynamic nail of FIG. 1, in accordance with an aspect of the present disclosure.
Figure 15:
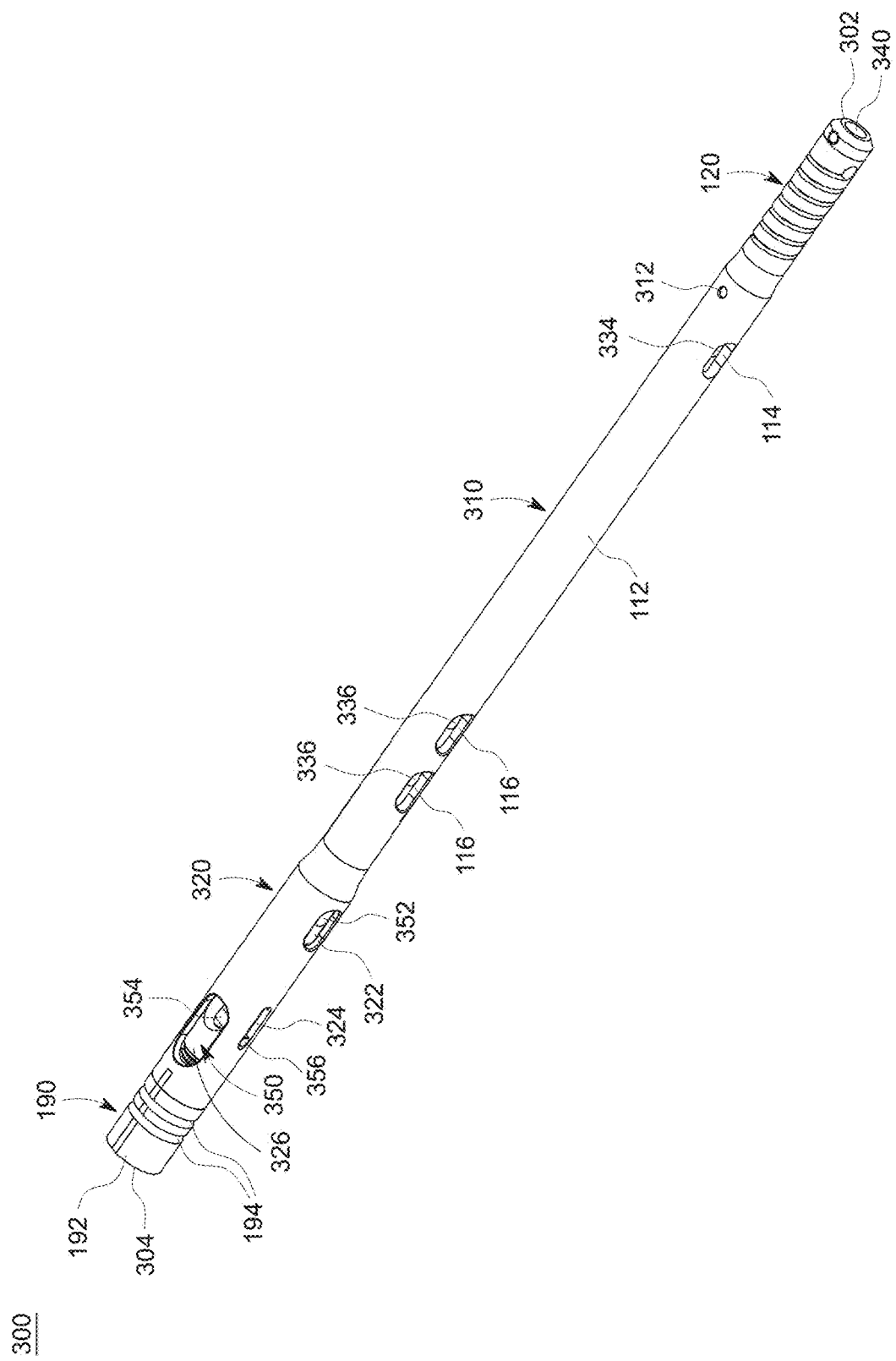
FIG. 15 is a first perspective view of another embodiment of a dynamic nail, in accordance with an aspect of the present disclosure.
Figure 16:
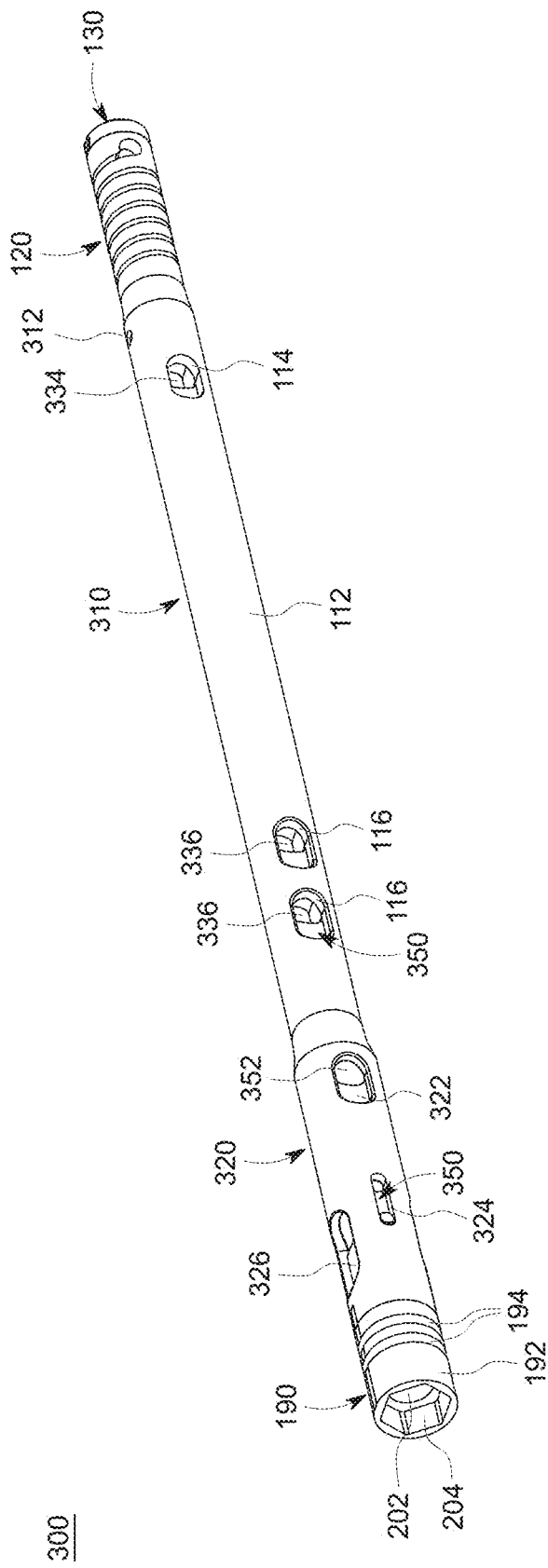
FIG. 16 is a second perspective view of the dynamic nail of FIG. 15, in accordance with an aspect of the present disclosure.

The distal end portion 140 of the first member 110 includes a shaft or body 142 coupled to the second end of the body portion 112. The distal end portion 140 may also include a distal or second through hole or fastener hole 144 positioned near the second end 104 of the implant 100. The through hole 144 may extend through the body 142 from one side to the other side perpendicular to the longitudinal axis of the first member 110. As shown in FIG. 14, the distal end portion 140 may also include a threaded portion 146 positioned on an interior surface of the through hole 122 of the first member 110.

With continued reference to FIGS. 3, 4, 13 and 14, the second member or inner rod 150 includes a body portion or shaft 152 with an inner rod clip 160 coupled to and extending away from a first end of the second member 150 and a distal end portion 170 coupled to and extending away from a second end of the second member 150. The second member 150 may also include a first or proximal through hole or fastener hole 154 for receiving a bone screw or bone fastener. The through hole 154 may be positioned, for example, near the inner rod clip 160. The through hole 154 may be positioned to align with the through hole 114 of the first member 110 when assembled. The second member 150 may further include at least one second through hole or fastener hole 156 positioned near the distal end portion 170. The second through holes 156 may be positioned to align with the second through holes 116 of the first member 110 when assembled. The second member 150 may also include at least one anti-rotation pin opening 158 configured or sized and shaped to receive an anti-rotation pin 106. The pin opening 158 may be, for example, positioned to align with the pin opening 118 to allow the pin 106 to be inserted through the pin opening 118 and pin opening 158 to secure the first member 110 to the second member 130.

Figure 3:
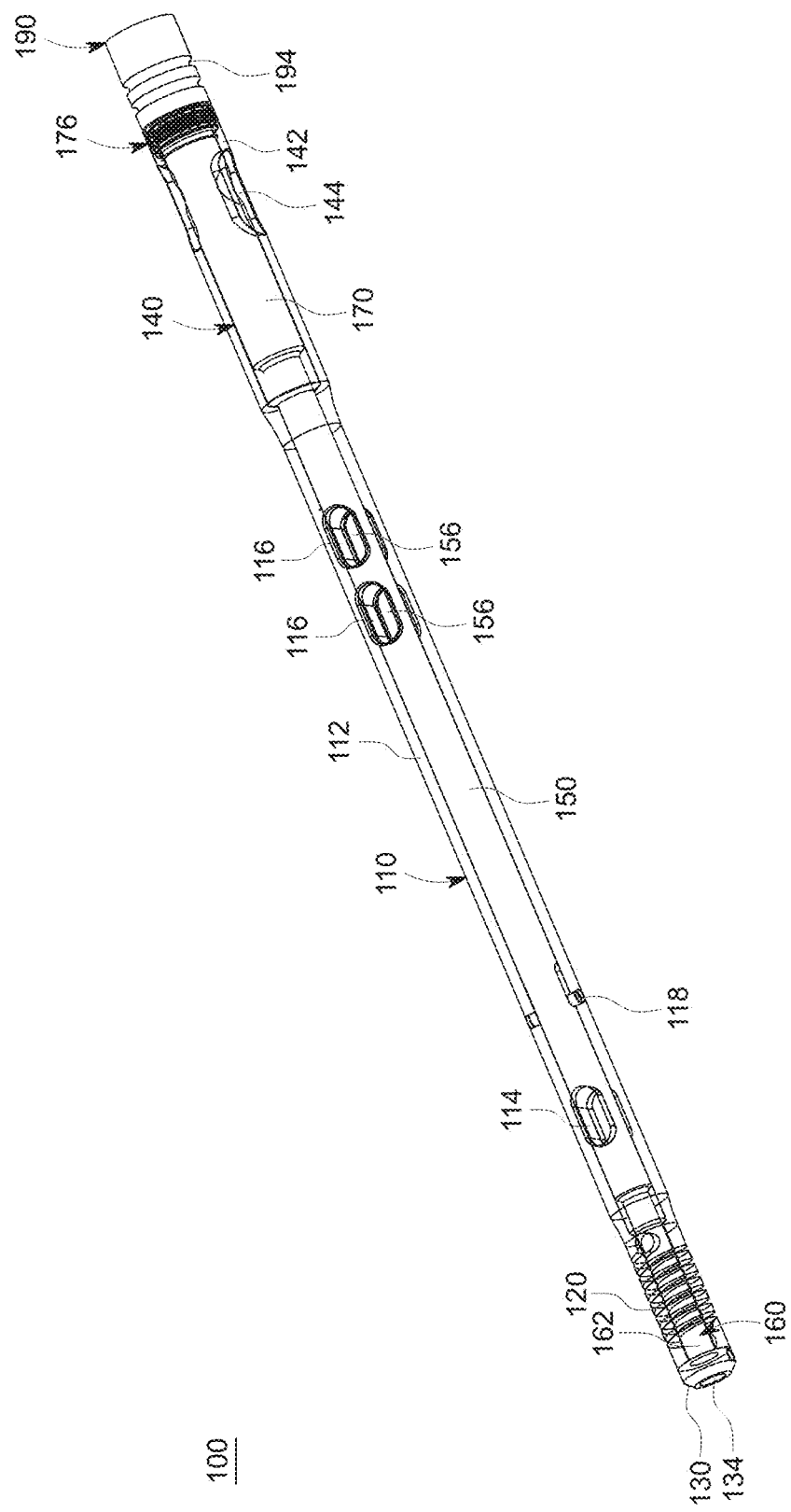
FIG. 3 is a third perspective view of the dynamic nail of FIG. 1 with a transparent body portion, in accordance with an aspect of the present disclosure.
Figure 4:
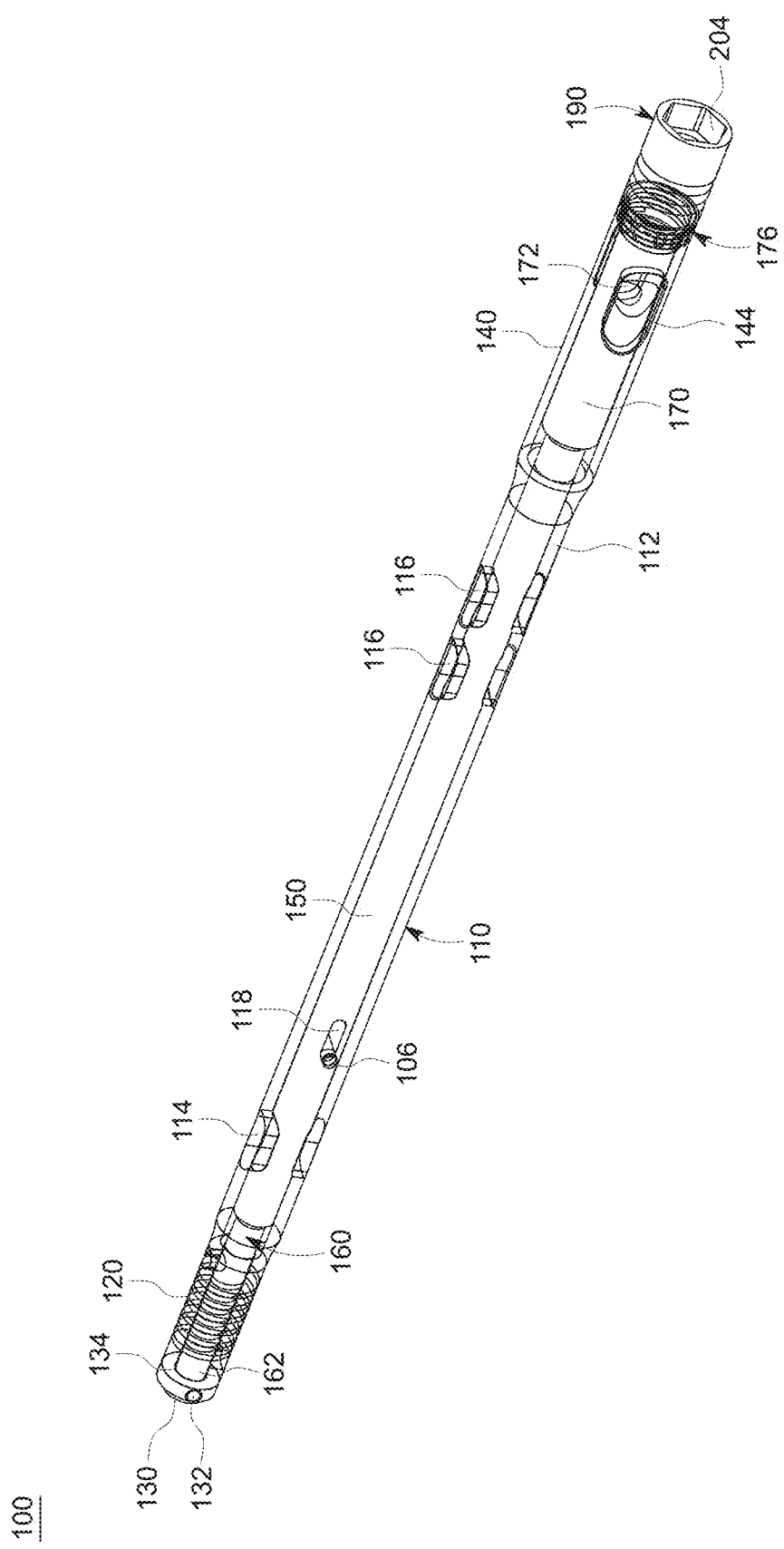
FIG. 4 is a fourth perspective view of the dynamic nail of FIG. 3, in accordance with an aspect of the present disclosure.
Figure 5:
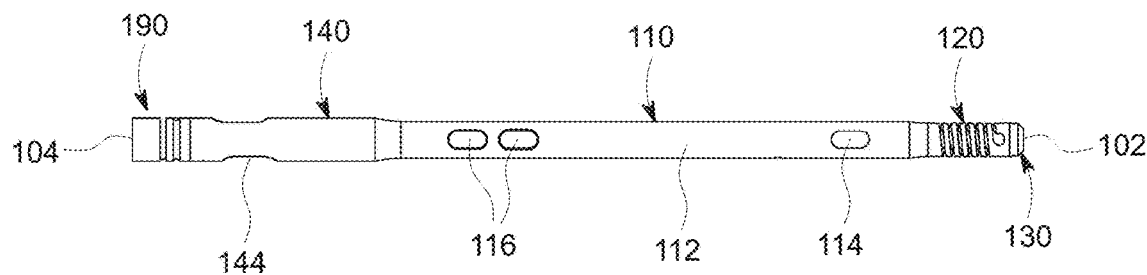
FIG. 5 is a first side view of the dynamic nail of FIG. 1, in accordance with an aspect of the present disclosure.
Figure 6:
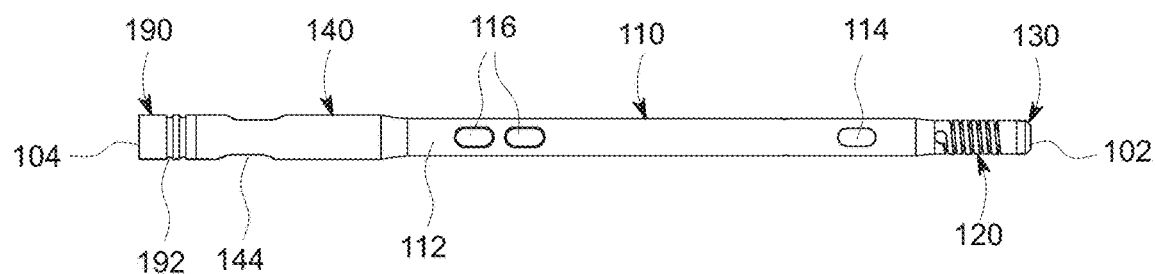
FIG. 6 is a second side view of the dynamic nail of FIG. 1, in accordance with an aspect of the present disclosure.
Figure 7:
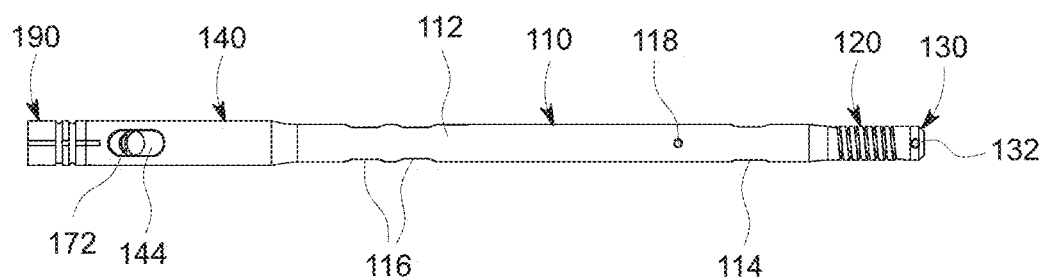
FIG. 7 is a third side view of the dynamic nail of FIG. 1, in accordance with an aspect of the present disclosure.
Figure 8:
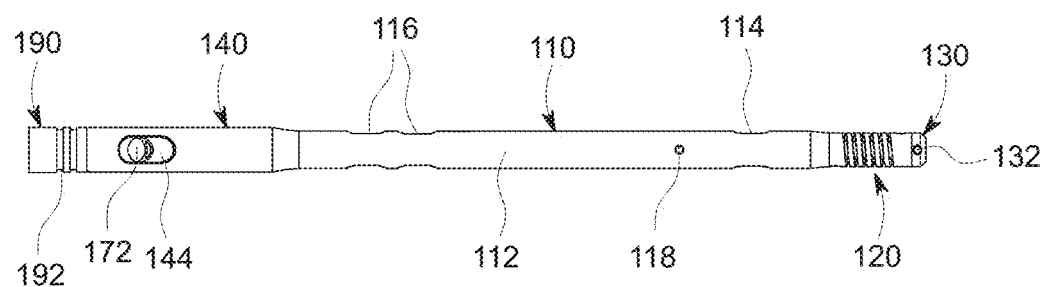
FIG. 8 is a fourth side view of the dynamic nail of FIG. 1, in accordance with an aspect of the present disclosure.
Figure 9:
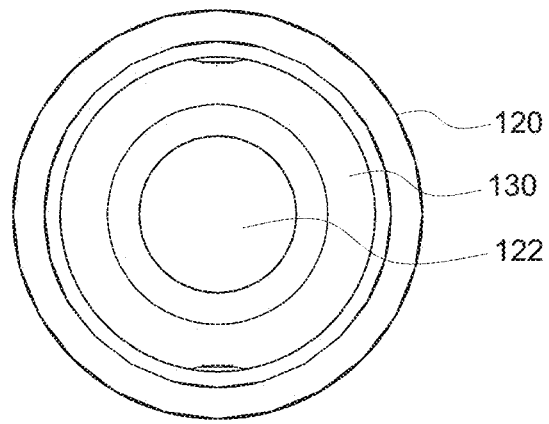
FIG. 9 is a first end view of the dynamic nail of FIG. 1, in accordance with an aspect of the present disclosure.
Figure 10:
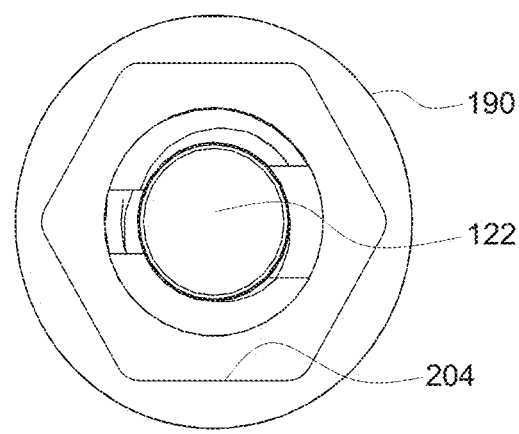
FIG. 10 is a second end view of the dynamic nail of FIG. 1, in accordance with an aspect of the present disclosure.
Figure 11:
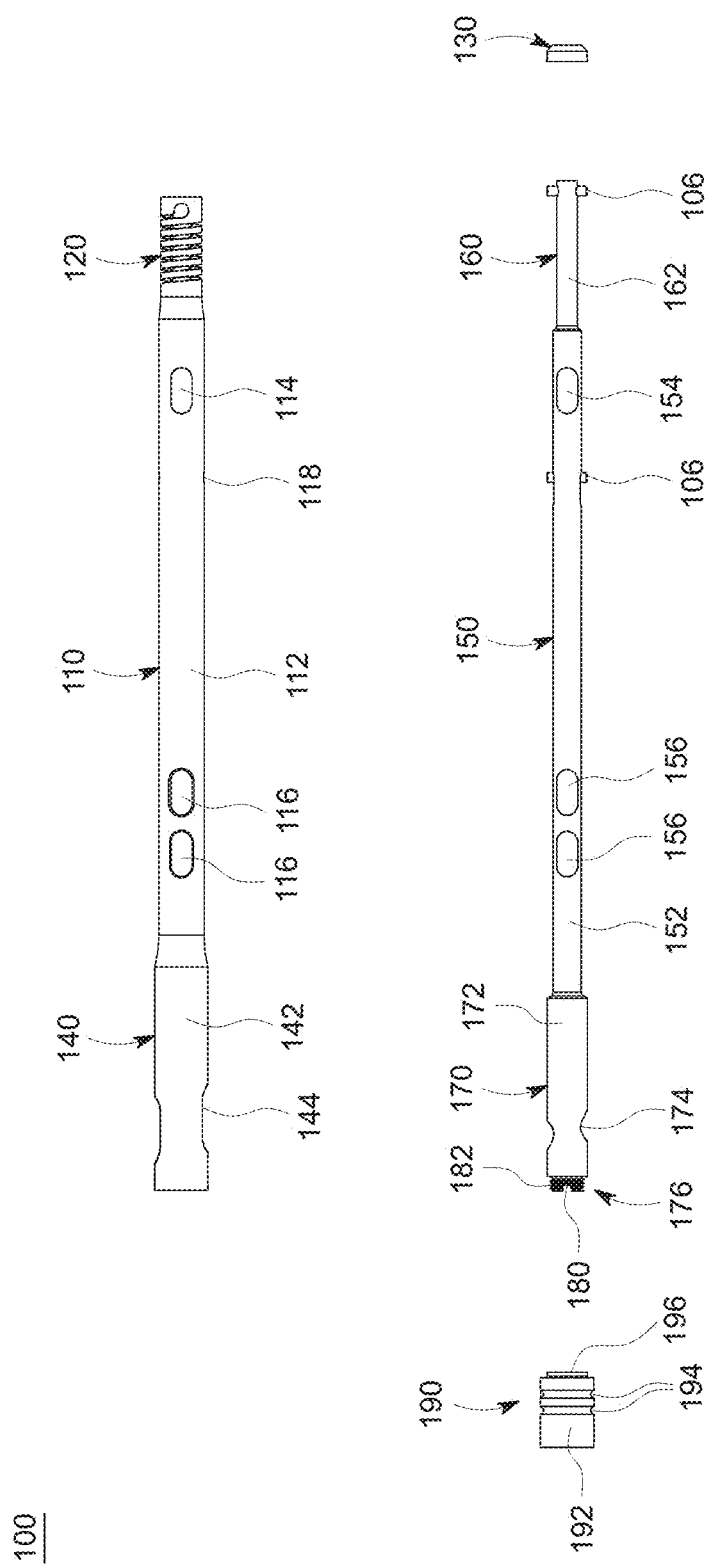
FIG. 11 is an exploded, first side view of the dynamic nail of FIG. 1, in accordance with an aspect of the present disclosure.
Figure 12:
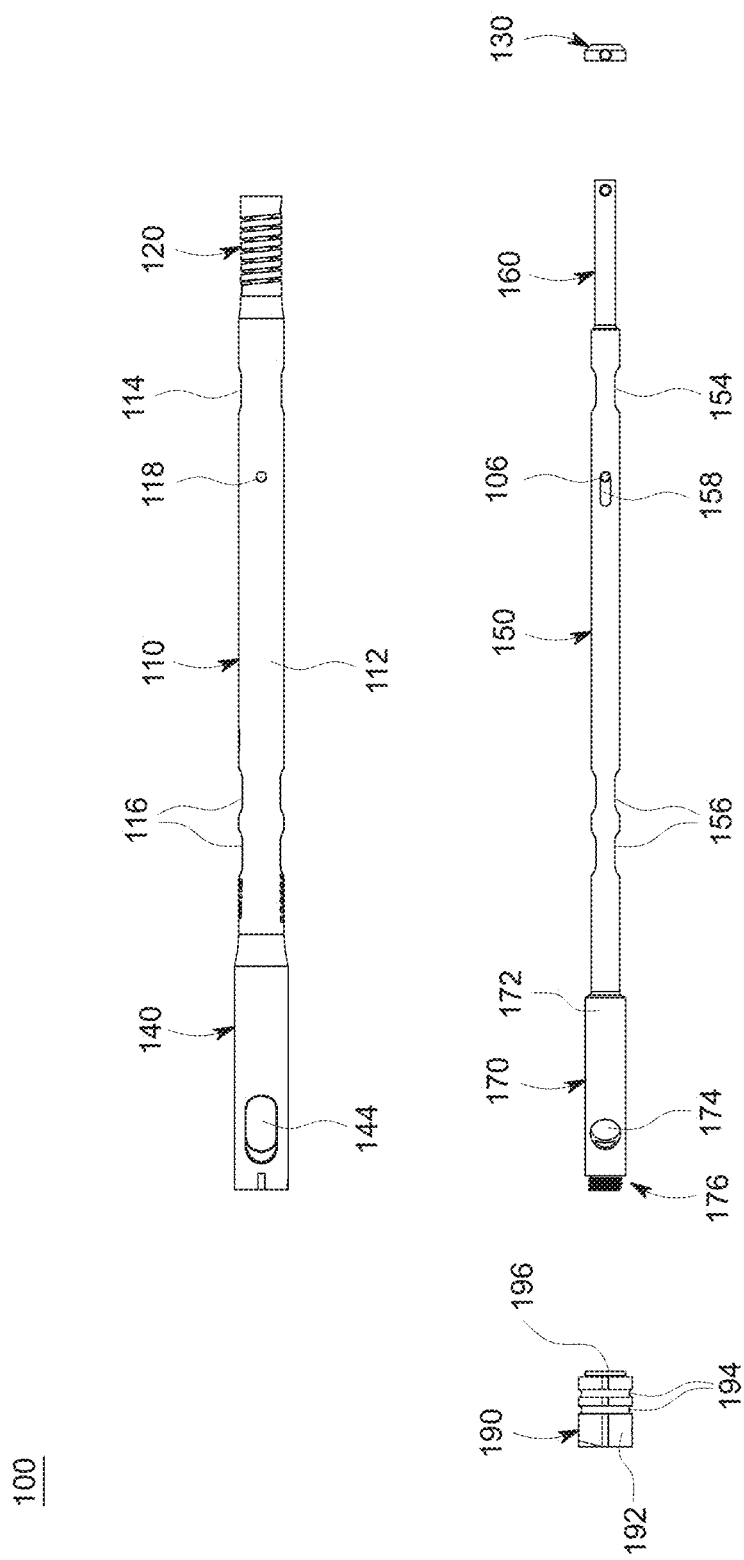
FIG. 12 is an exploded, second side view of the dynamic nail of FIG. 1, in accordance with an aspect of the present disclosure.
Figure 13:
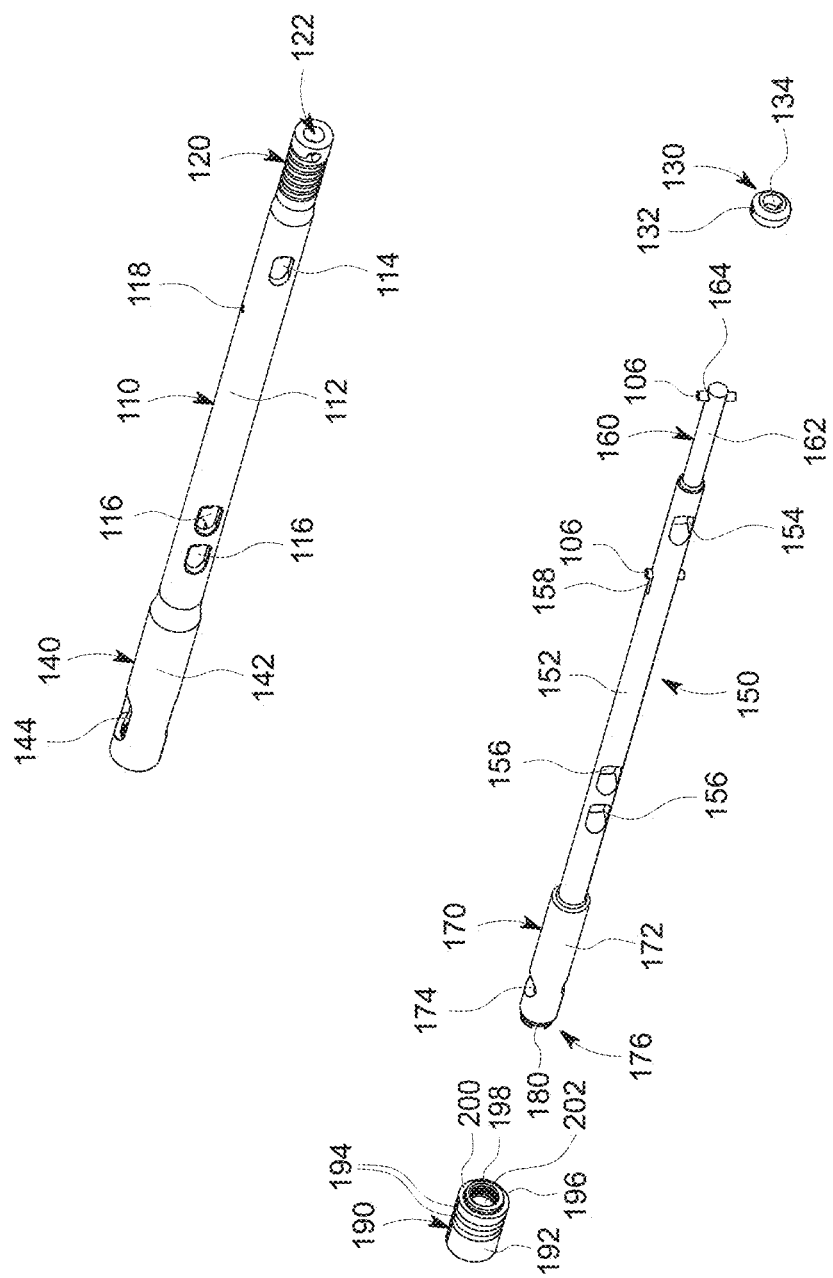
FIG. 13 is an exploded, first perspective view of the dynamic nail of FIG. 1, in accordance with an aspect of the present disclosure.

As shown in FIGS. 3, 4, 9, 13 and 14, the inner rod clip 160 includes a base portion 162 coupled to and extending away from the body portion 152. The inner rod clip 160 may also include an anti-rotation pin opening 164 extending through the inner rod clip 160 and configured or sized and shaped to receive a pin 106. When assembled, at least a first portion of the base portion 162 is positioned within the through hole 122 and surrounded by the deformable member 120 and at least a second portion of the base portion 162 is positioned within the through hole 134 of the coupling member 130, as shown in FIGS. 3 and 4. In an alternative embodiment, the inner rod clip 160 may include a slot (not shown) machined into it to allow for flexible tines (not shown). Once the tines of the inner rod clip 160 engage the outer sheath 110, the tines can help to prevent dissociation. The tines also transfer and hold the forces of the external spring 120.

The distal end portion 170 includes a shaft or body 172 extending away from the body portion 152 at an end opposite the base portion 162. The distal end portion 170 also includes a second or distal through hole or fastener hole 174 for receiving a bone screw or bone fastener. The distal end portion 170 further includes a coupling portion 176. The coupling portion 176 includes an opening 178 extending into the distal end portion 170 from the second end. The opening 178 may include internal threads along at least a portion of the opening. The coupling portion 176 may also include alignment recesses 180 inset into the coupling portion 176 from the second end. The alignment recesses 180 may engage corresponding alignment protrusions in the tension screw 190. The coupling portion 176 may also include external threads 182 surrounding the circumference of the second end.

With continued reference to FIGS. 3, 4, 13 and 14, the tension screw 190 may include a body portion 192 with at least one groove 194 inset into the exterior surface of the body portion 192. The tension screw 190 may also include a coupling protrusion 196 extending away from the first end of the tension screw 190. The coupling protrusion 196 may include an interior threaded portion 198 positioned along the interior surface of the through hole 202 and an exterior threaded portion 200 surrounding the circumference of the exterior surface of the protrusion 196. The tension screw 190 may also include a tool engagement opening or drive opening 204 to receive a tool to remove the pre-loaded compression from the implant 100. The tension screw 190 holds the proximal external spring 120 in compression. The tension screw 190 may be, for example, releasably couplable with the implant 100 such that manipulation and/or release of the tension screw 190 actuates the proximal external spring 120 from a pre-loaded (e.g., compressed) position to a loaded (e.g., at least partially compressed) position. Thus, the implant 100 may be ready for insertion into a patient in a "pre-loaded" position, which includes compression of the deformable member 120 and positioning the anti-rotation pins 106 at the bottom of their respective slots.

Referring now to FIGS. 15-30, a dynamic nail, a dual spring dynamic nail or dual spring implant 300 is shown. The nail 300 has a first end 302, a second end 304 and a through hole 306 extending through the nail 300 along a longitudinal axis. The implant 300 is an IM nail or crossing screw. The implant 300 includes a first member or outer sheath 310, a second member or inner rod 330, a coupling member 130 to secure the first member 310 to the second member 330 at the first or proximal end 302, and a tension screw 190 to secure the first member 310 to the second member 330 at the second or distal end 304. The coupling member 130 and the tension screw 190 are of the type described above with reference to implant 100, which will not be described again here for brevity sake. The tension screw 190 may be, for example, releasably couplable with the implant 300 such that manipulation and/or release of the tension screw 190 actuates the proximal external spring 120 from a pre-loaded (e.g., compressed) position to a loaded (e.g., at least partially compressed) position.

Figure 30:
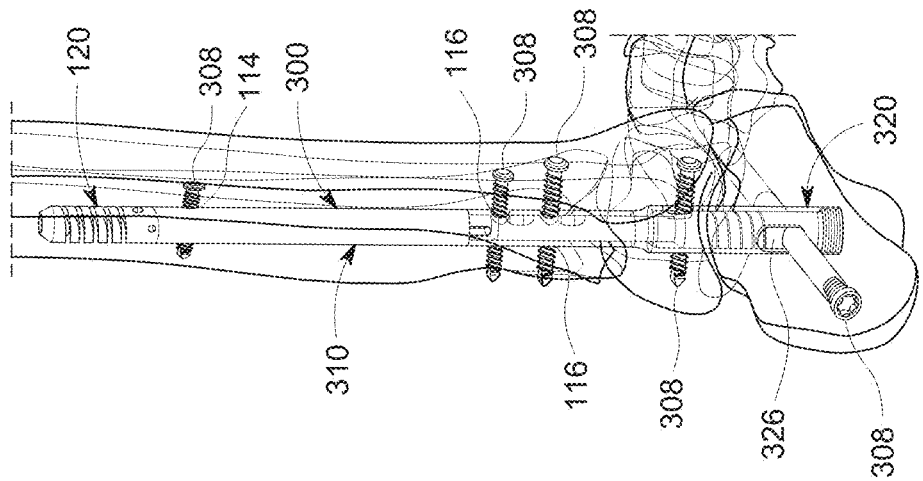
FIG. 30 is a perspective view of a larger embodiment of the dynamic nail of FIGS. 15-28 inserted into a patient's lower extremity, in accordance with an aspect of the present disclosure.

With continued reference to FIGS. 15-30, the first member 310 includes a body portion 112, a deformable member 120 coupled to a first end of the body portion 112, and a distal end portion 320 coupled to a second end of the body portion 112. The first member 310 also includes a first or proximal through hole or fastener hole 114 positioned near the deformable member 120 and at least one second through hole or fastener hole 116 positioned near the distal end portion 320. The holes 114, 116 may be, for example, elongated or oval holes. The holes 114, 116 may extend through the body portion 112 from one side to the other perpendicular to the longitudinal axis of the first member 310. The holes 114, 116 may be, for example, sized and shaped or configured to receive a bone screw or bone fastener 308, as shown in FIGS. 29 and 30. The body portion 112 may also include at least one anti-rotation pin opening 312 extending through the body portion 112 from one side to the other side and positioned between the hole 114 and the deformable member 120. The pin opening 312 is, for example, sized and shaped or configured to receive an anti-rotation pin 106. The first member 310 may also include a through hole 306 extending through the first member 310 along the longitudinal axis of the first member 310.

Figure 28:
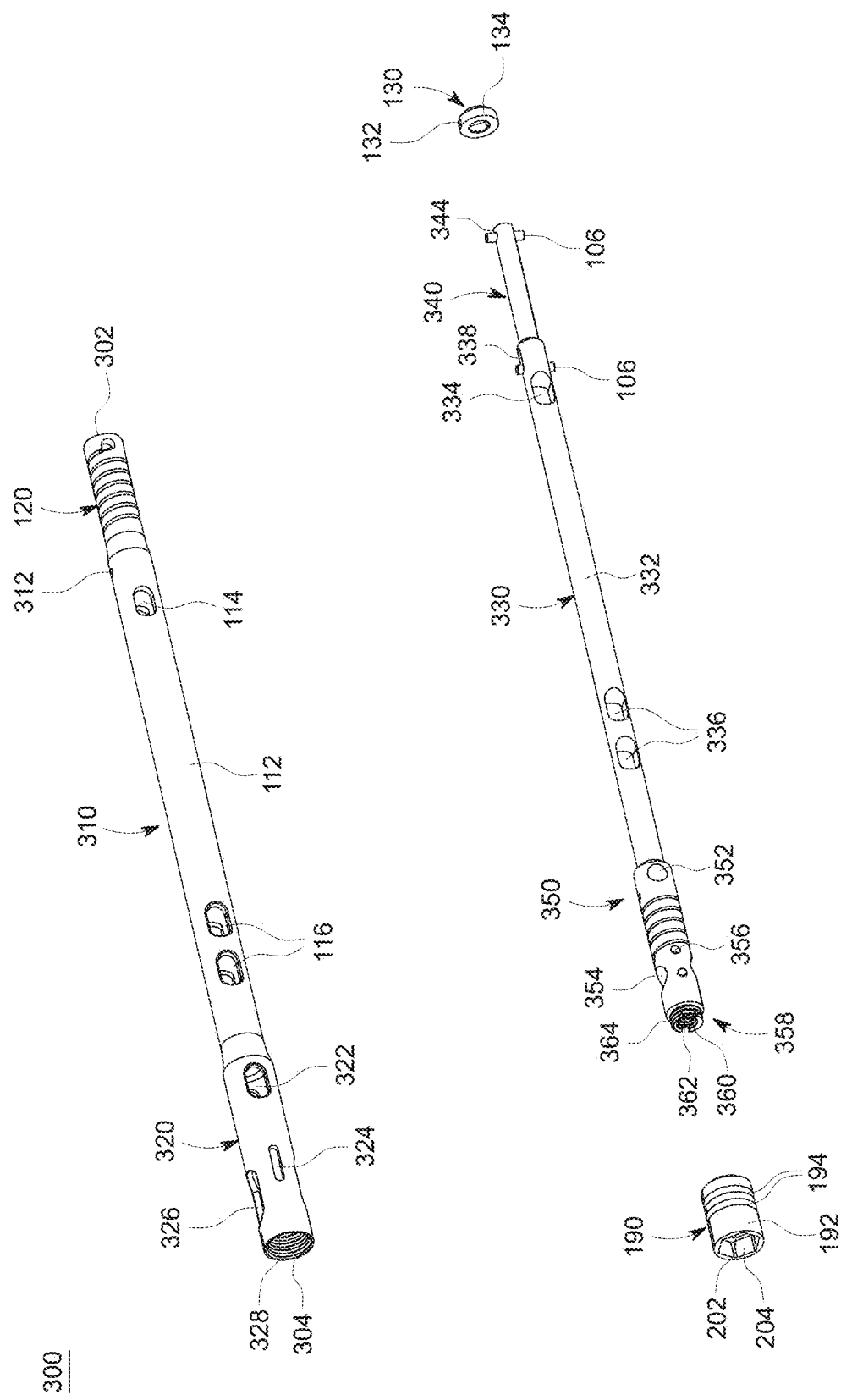
FIG. 28 is an exploded, second perspective view of the dynamic nail of FIG. 15, in accordance with an aspect of the present disclosure.
Figure 29:
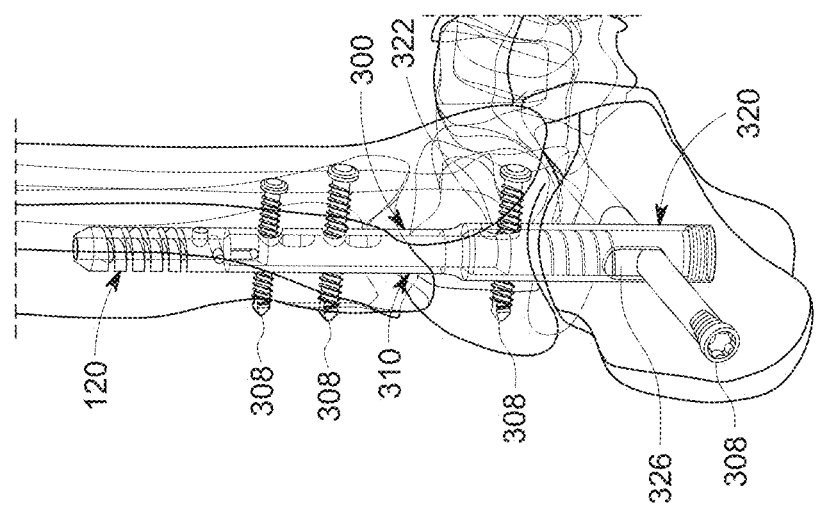
FIG. 29 is a perspective view of the dynamic nail of FIGS. 15-28 inserted into a patient's lower extremity, in accordance with an aspect of the present disclosure.
Figure 31:
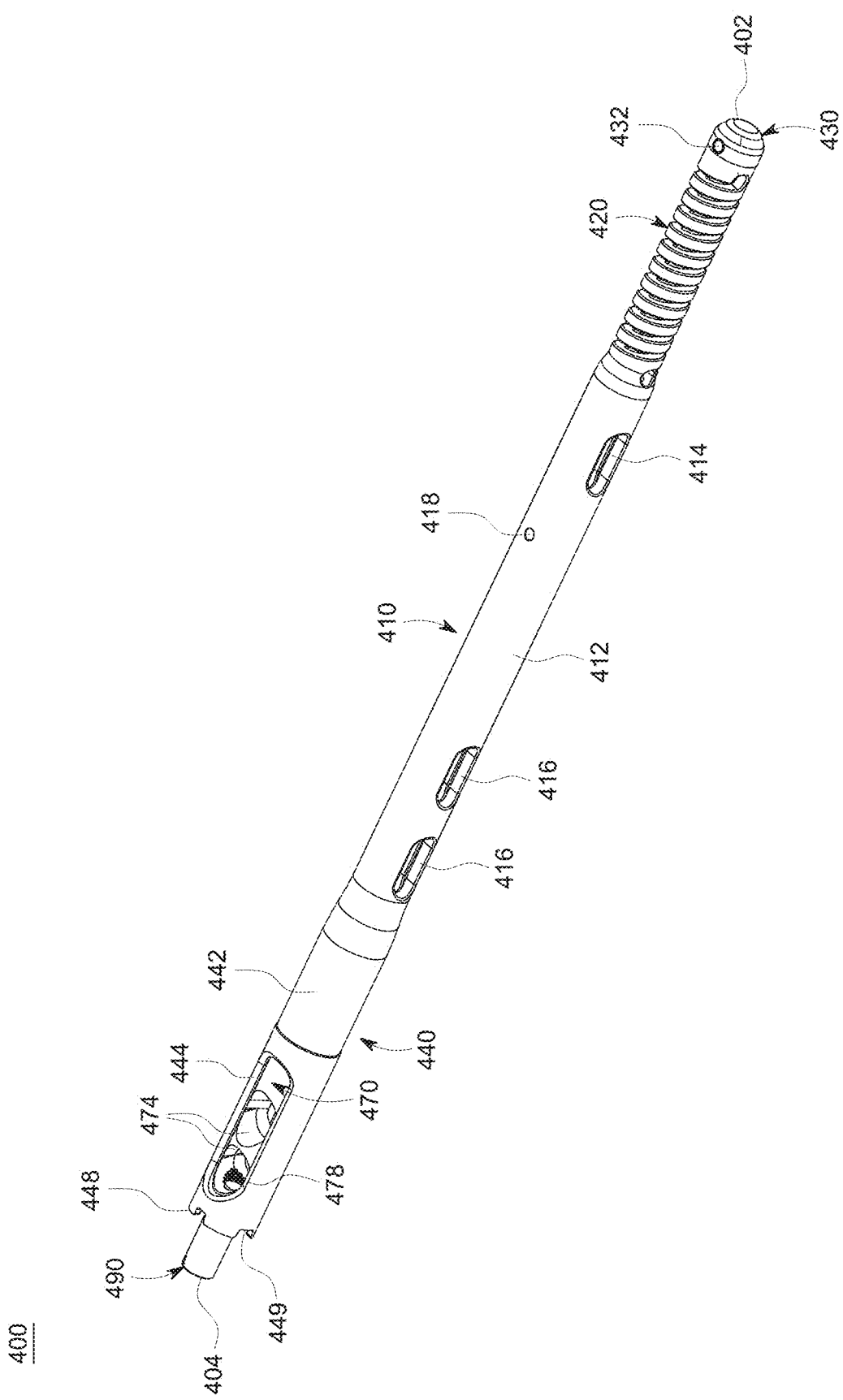
FIG. 31 is a first perspective view of another embodiment of a dynamic nail in a compressed position, in accordance with an aspect of the present disclosure.
Figure 32:
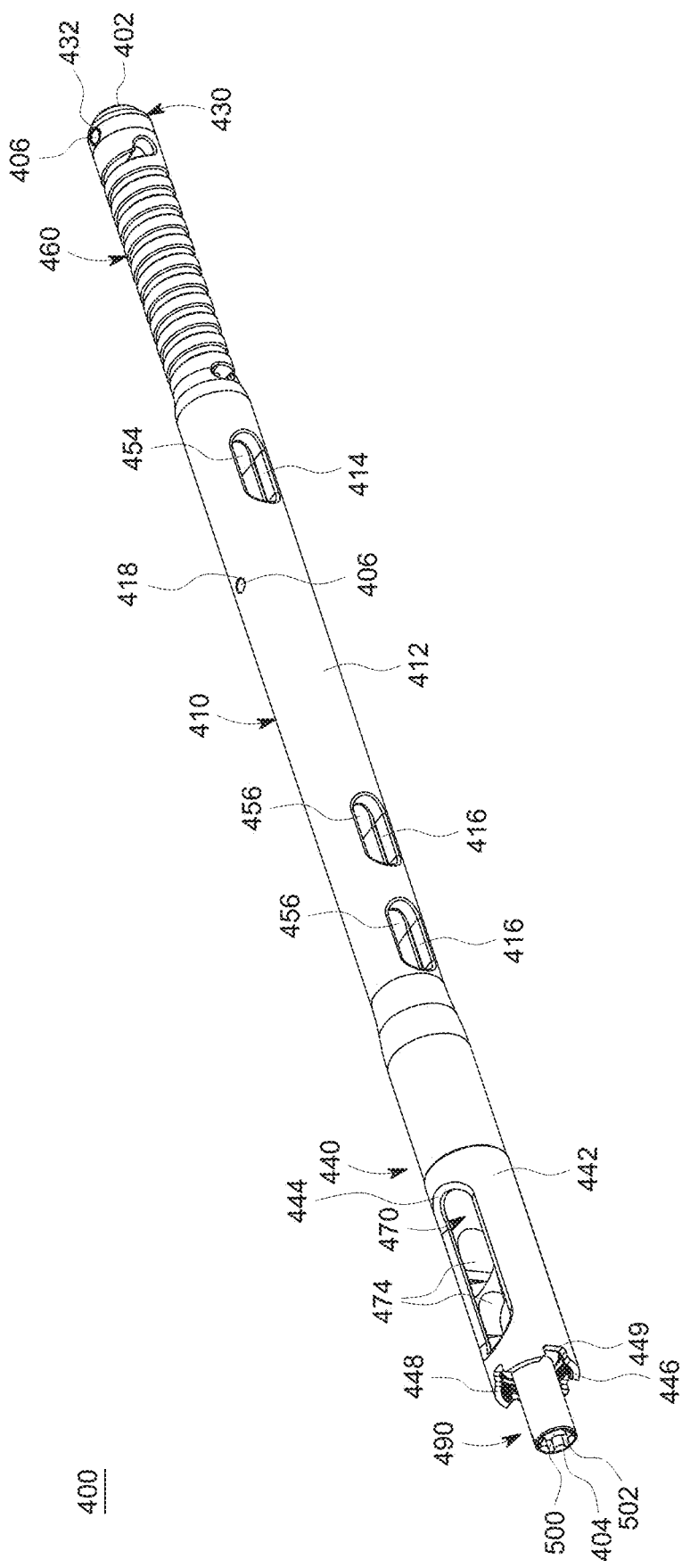
FIG. 32 is a second perspective view of the dynamic nail of FIG. 31, in accordance with an aspect of the present disclosure.

The distal end portion 320 of the first member 310 is coupled to the second end of the body portion 112, as shown in FIGS. 17, 18 and 25-28. The distal end portion 320 may also include a first through hole or fastener hole 322 positioned near the body portion 112 of the implant 300. The distal end portion 320 may further include a second through hole or fastener hole 326 that may extend through the distal end portion 320 from one side to the other side perpendicular to the longitudinal axis of the first member 310. In addition, the distal end portion 320 may include an anti-rotation pin opening 324 extending through the distal end portion 320 from one side to the other side. The pin opening 324 is, for example, sized and shaped or configured to receive an anti-rotation pin 106. As shown in FIG. 28, the distal end portion 320 may also include a threaded portion 328 positioned on an interior surface of the through hole 306 of the first member 310.

With continued reference to FIGS. 17, 18 and 25-28, the second member or inner rod 330 includes a shaft or body portion 332 with an inner rod clip 340 coupled to and extending away from a first end of the second member 330 and a second deformable member, second spring, or internal spring 350 coupled to and extending away from a second end of the body portion 332 of the second member 330. The body portion 332 of the second member 330 may also include a first or proximal through hole or fastener hole 334 for receiving a bone screw or bone fastener 308. The through hole 334 may be positioned, for example, near the inner rod clip 340. The through hole 334 may be positioned to align with the through hole 114 of the first member 310 when assembled. The second member 330 may further include at least one second through hole or fastener hole 336 positioned near the second deformable member 350. The second through holes 336 may be positioned to align with the second through holes 116 of the first member 310 when assembled. The second member 330 may also include at least one anti-rotation pin opening 338 configured or sized and shaped to receive an anti-rotation pin 106. The pin opening 338 may be, for example, positioned to align with the pin opening 312 to allow the pin 106 to be inserted through the pin opening 312 and pin opening 338 to secure the first member 310 to the second member 330.

Figure 17:
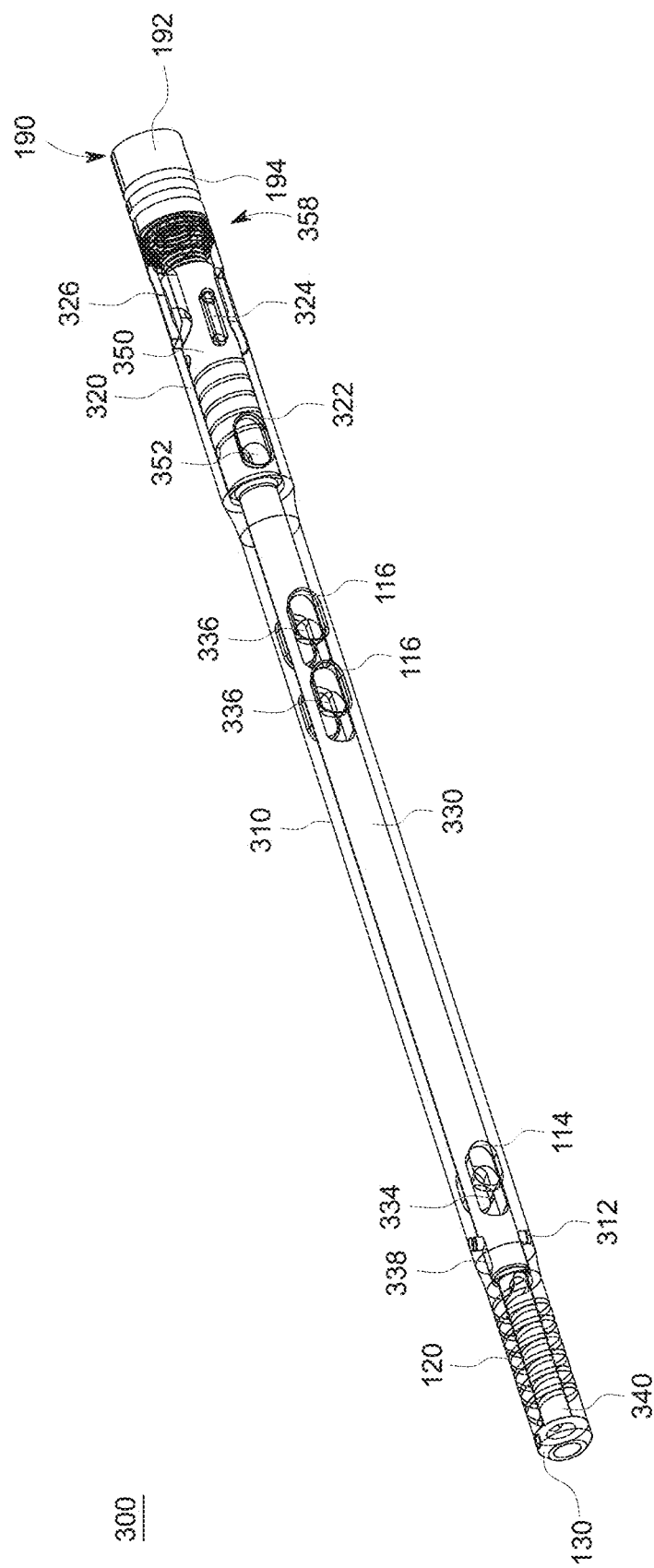
FIG. 17 is a third perspective view of the dynamic nail of FIG. 15 with a transparent body portion, in accordance with an aspect of the present disclosure.
Figure 18:
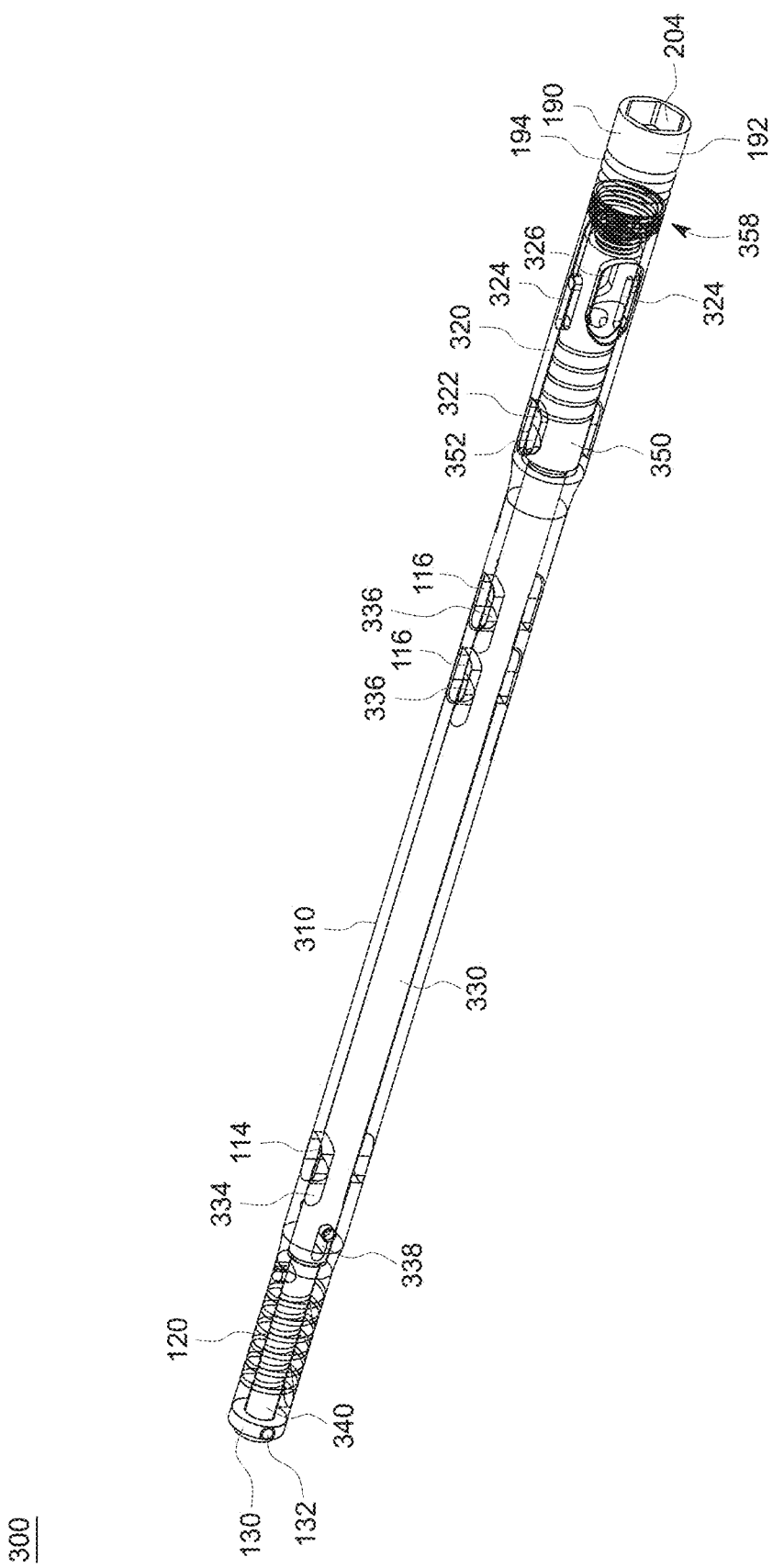
FIG. 18 is a fourth perspective view of the dynamic nail of FIG. 17, in accordance with an aspect of the present disclosure.
Figure 19:
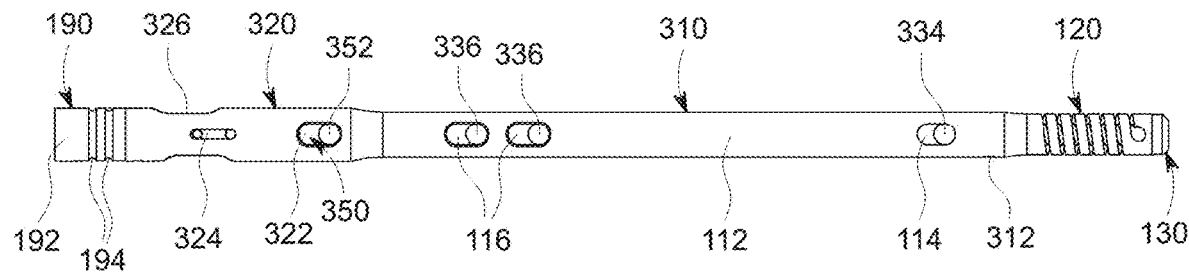
FIG. 19 is a first side view of the dynamic nail of FIG. 15, in accordance with an aspect of the present disclosure.
Figure 20:
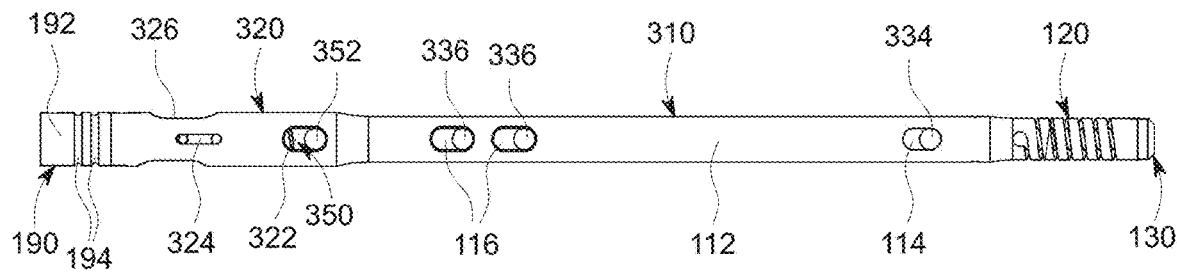
FIG. 20 is a second side view of the dynamic nail of FIG. 15, in accordance with an aspect of the present disclosure.
Figure 21:
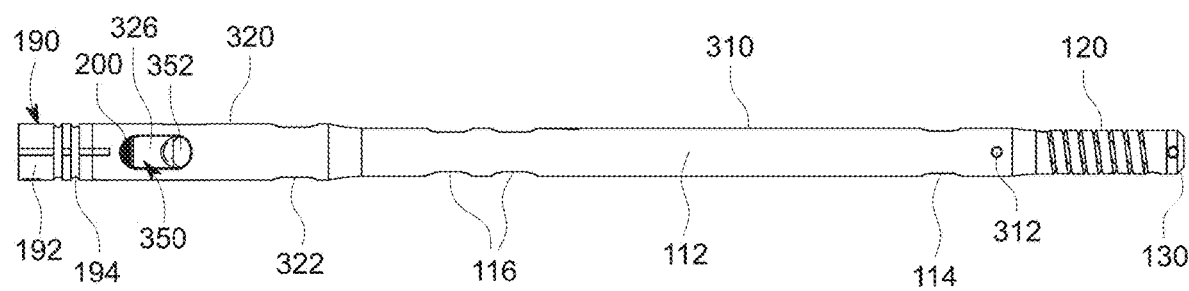
FIG. 21 is a third side view of the dynamic nail of FIG. 15, in accordance with an aspect of the present disclosure.
Figure 22:
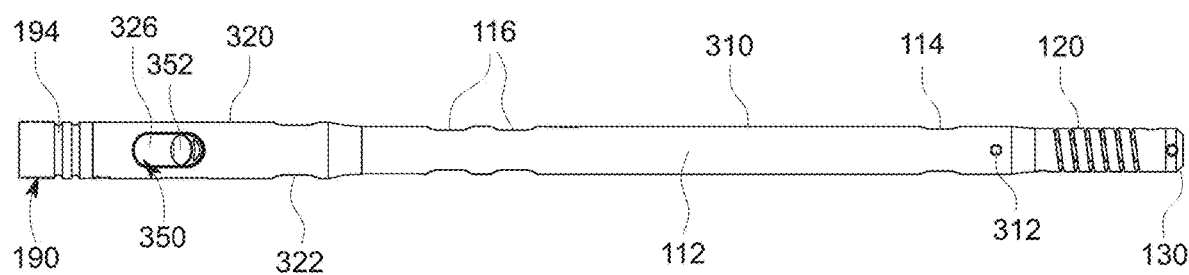
FIG. 22 is a fourth side view of the dynamic nail of FIG. 15, in accordance with an aspect of the present disclosure.
Figure 23:
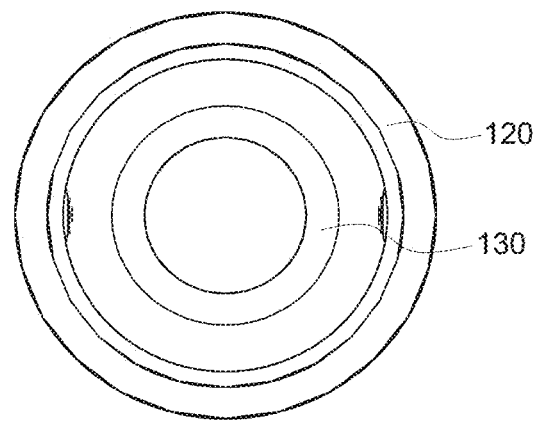
FIG. 23 is a first end view of the dynamic nail of FIG. 15, in accordance with an aspect of the present disclosure.
Figure 24:
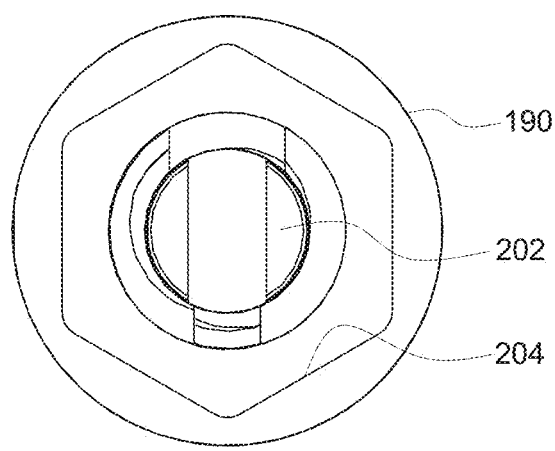
FIG. 24 is a second end view of the dynamic nail of FIG. 15, in accordance with an aspect of the present disclosure.
Figure 25:
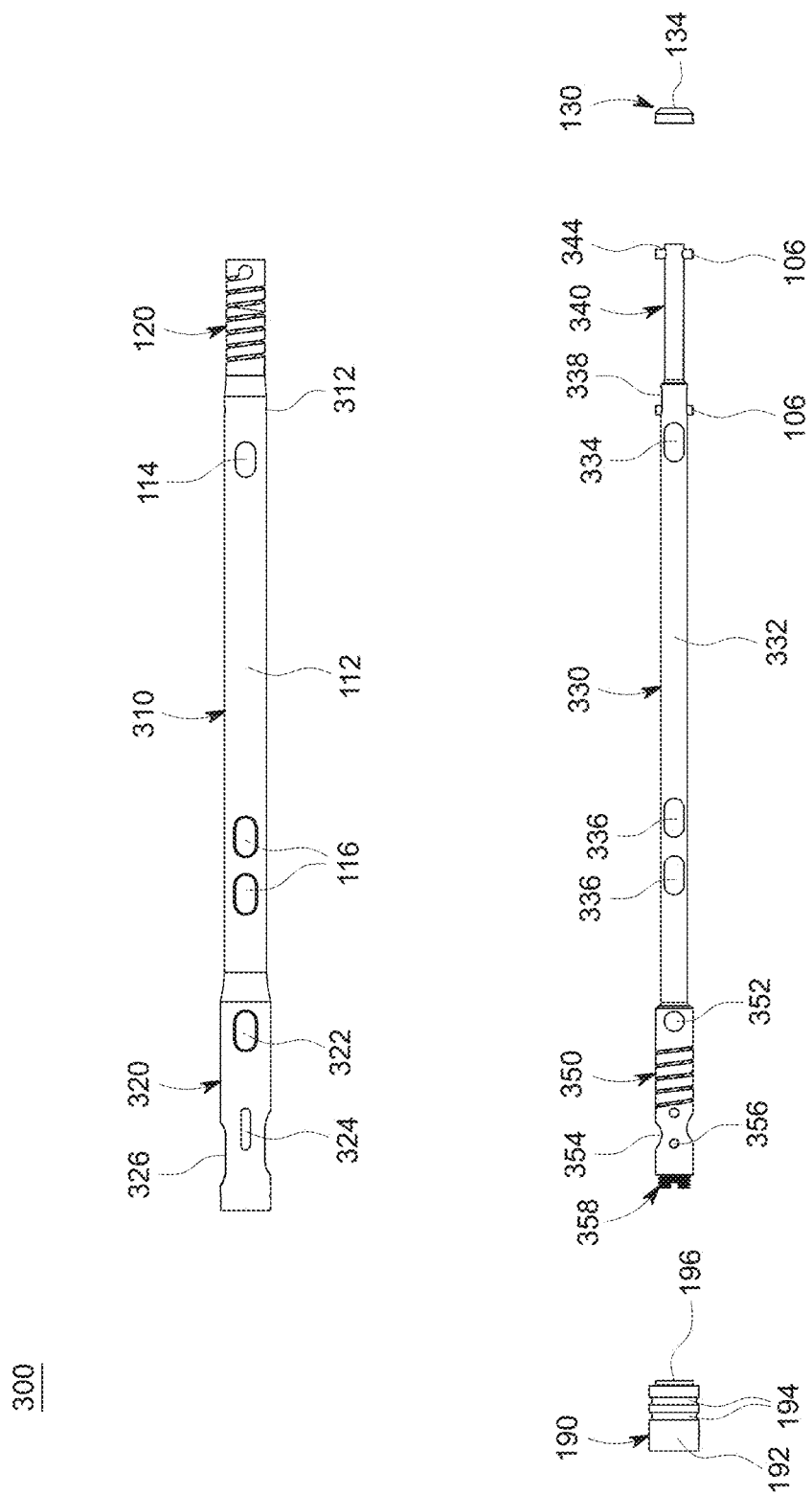
FIG. 25 is an exploded, first side view of the dynamic nail of FIG. 15, in accordance with an aspect of the present disclosure.
Figure 26:
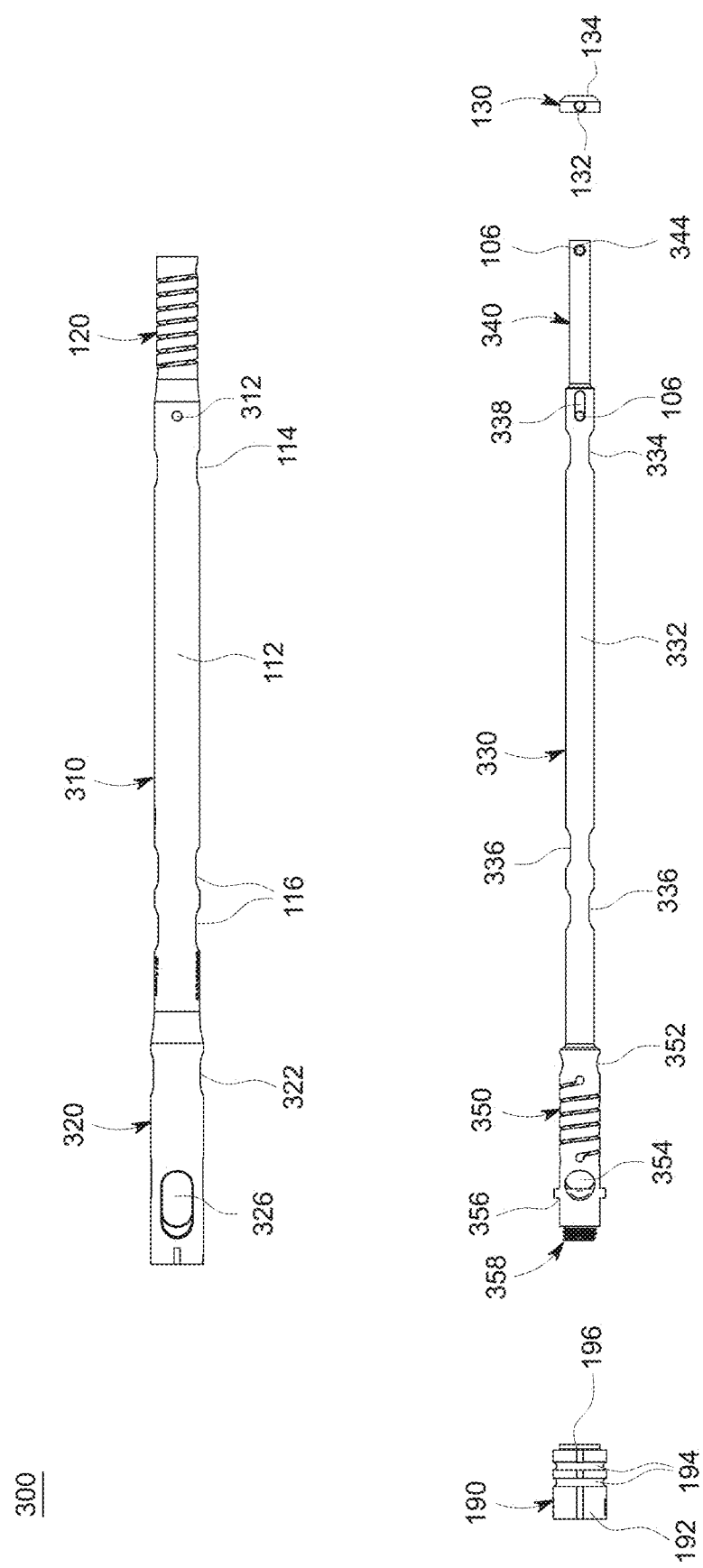
FIG. 26 is an exploded, second side view of the dynamic nail of FIG. 15, in accordance with an aspect of the present disclosure.
Figure 27:
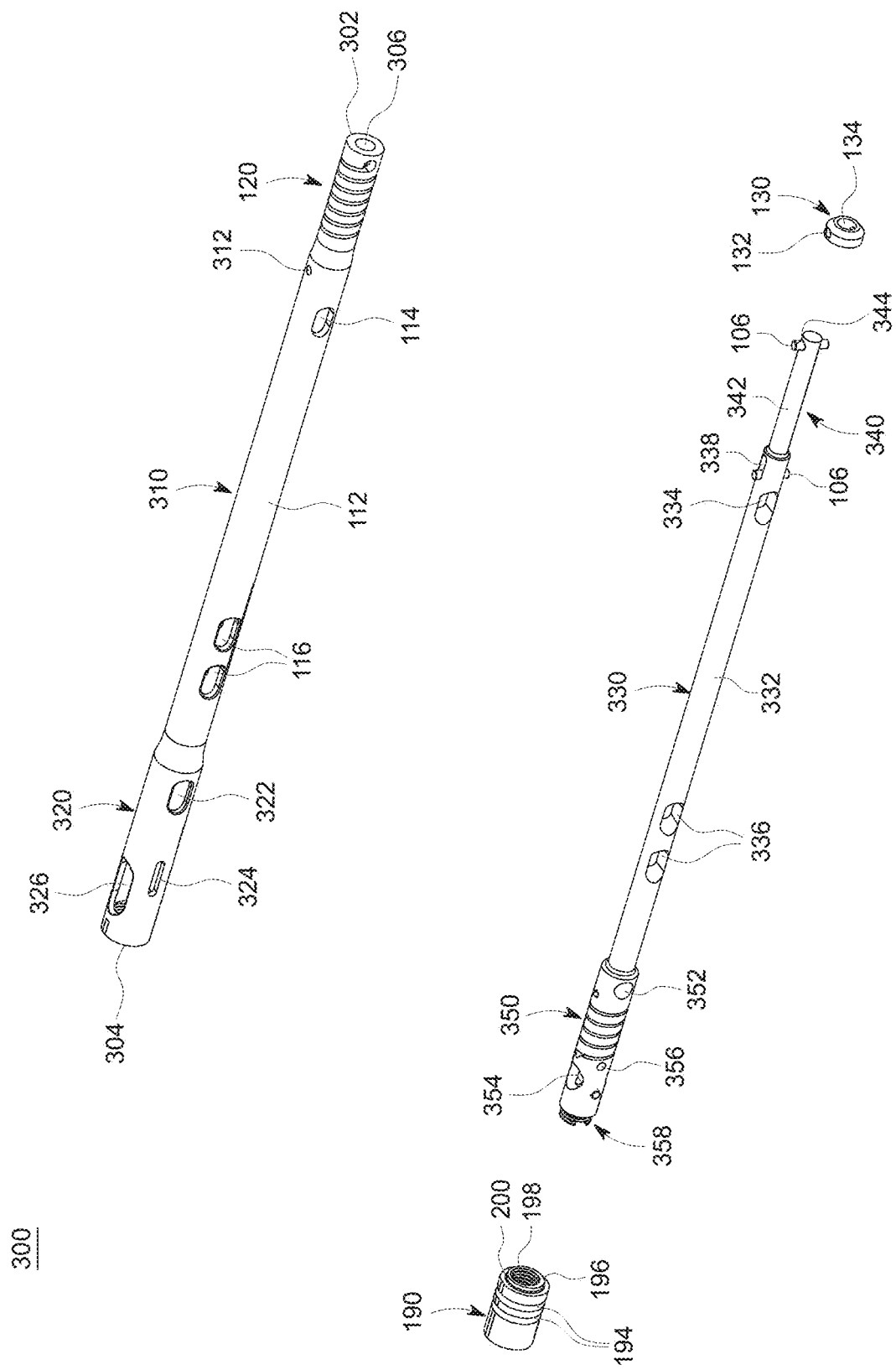
FIG. 27 is an exploded, first perspective view of the dynamic nail of FIG. 15, in accordance with an aspect of the present disclosure.

As shown in FIGS. 17, 18 and 25-28, the inner rod clip 340 includes a base portion 342 coupled to and extending away from the body portion 332. The inner rod clip 340 may also include an anti-rotation pin opening 344 extending through the inner rod clip 340 and configured or sized and shaped to receive a pin 106. When assembled, the base portion 342 is positioned within the through hole 306 of the first member 310 and surrounded by the deformable member 120, as shown in FIGS. 17 and 18. In an alternative embodiment, the inner rod clip 340 may include a slot (not shown) machined into it to allow for flexible tines (not shown). Once the tines of the inner rod clip 340 engage the outer sheath 310, the tines can help to prevent dissociation. The tines also transfer and hold the forces of the external and internal springs 120, 350.

The second deformable member 350 is a helical cut, machined spring. The helical spring 350 is cut into, one piece, or integral with the inner rod 330 of the nail 300. The spring 350 may include a first through hole or fastener hole 352 extending through the spring 350 from one side to the other side and a second through hole or fastener hole 354 extending through the spring 350 from the one side to the other side. The spring 350 may also include an anti-rotation pin opening 356 extending through the spring 350 from one side to the other side and positioned between the first through hole 352 and the second through hole 354. The second spring 350 may also include a coupling portion 358 positioned on the second or distal end of the second member 330. The coupling portion 358 may include an opening 360 with internal threads positioned on the interior surface of the opening 360. The coupling portion 358 also includes alignment recesses 362 inset into the second end of the spring 350. The alignment recesses 362 may engage corresponding alignment protrusions in the tension screw 190. The coupling portion 358 may also include external threads 364 surrounding the circumference of the second end.

Referring now to FIGS. 31-44, another implant 400 is shown. The implant 400 may be, for example, a dynamic nail, a dynamic nail, a single spring dynamic nail, IM nail, or crossing screw. The implant 400 includes a first member or outer sheath 410, a second member or inner rod 450, a coupling member 430 to secure the first member 410 to the second member 450 at the first or proximal end 402, and a tension screw 490 to secure the first member 410 to the second member 450 at the second or distal end 404.

With continued reference to FIGS. 31-44, the first member 410 includes a body portion or shaft 412, a deformable member 420 coupled to a first end of the body portion 412, and a distal end portion 440 coupled to a second end of the body portion 412. The first member 410 also includes a first or proximal through hole or fastener hole 414 positioned near the deformable member 420 and at least one second through hole or fastener hole 416 positioned near the distal end portion 440. The holes 414, 416 may be, for example, elongated or oval holes. The holes 414, 416 may extend through the body portion 412 from one side to the other side and may be oriented perpendicular to the longitudinal axis of the first member 410. The holes 414, 416 may be, for example, sized and shaped or configured to receive a bone screw or bone fastener. The body portion 412 may also include at least one anti-rotation pin opening 418 extending through the body portion 412 from one side to the other side. The pin opening 418 is, for example, sized and shaped or configured to receive an anti-rotation pin 406. The pin opening 418 may extend through the body portion 412, for example, perpendicular to the holes 414, 416. The first member 410 may also include a through hole 422 extending through the first member 410 along the longitudinal axis of the first member 410.

As shown in FIGS. 31-38 and 41-44, the deformable member, spring or proximal external spring member 420 is coupled to the first end of the body portion 412. When inserted into a patient, the proximal external spring 420 is positioned anatomically inside the tibia. The spring 420 may be inserted, for example, in a first compressed position and once implantation is complete, the spring 420 may move to at least one second partially compressed position. As depicted, the deformable member 420 is, for example, a helical cut, machined spring. The helical spring 420 may be, for example, cut into, one piece, or integral with the outer sheath 410 of the nail 400. The spring 420 may be compressed to provide stored energy required to apply a compressive force to the tibio-talar joint by "pulling" the talus toward the tibia once implanted.

Figure 44:
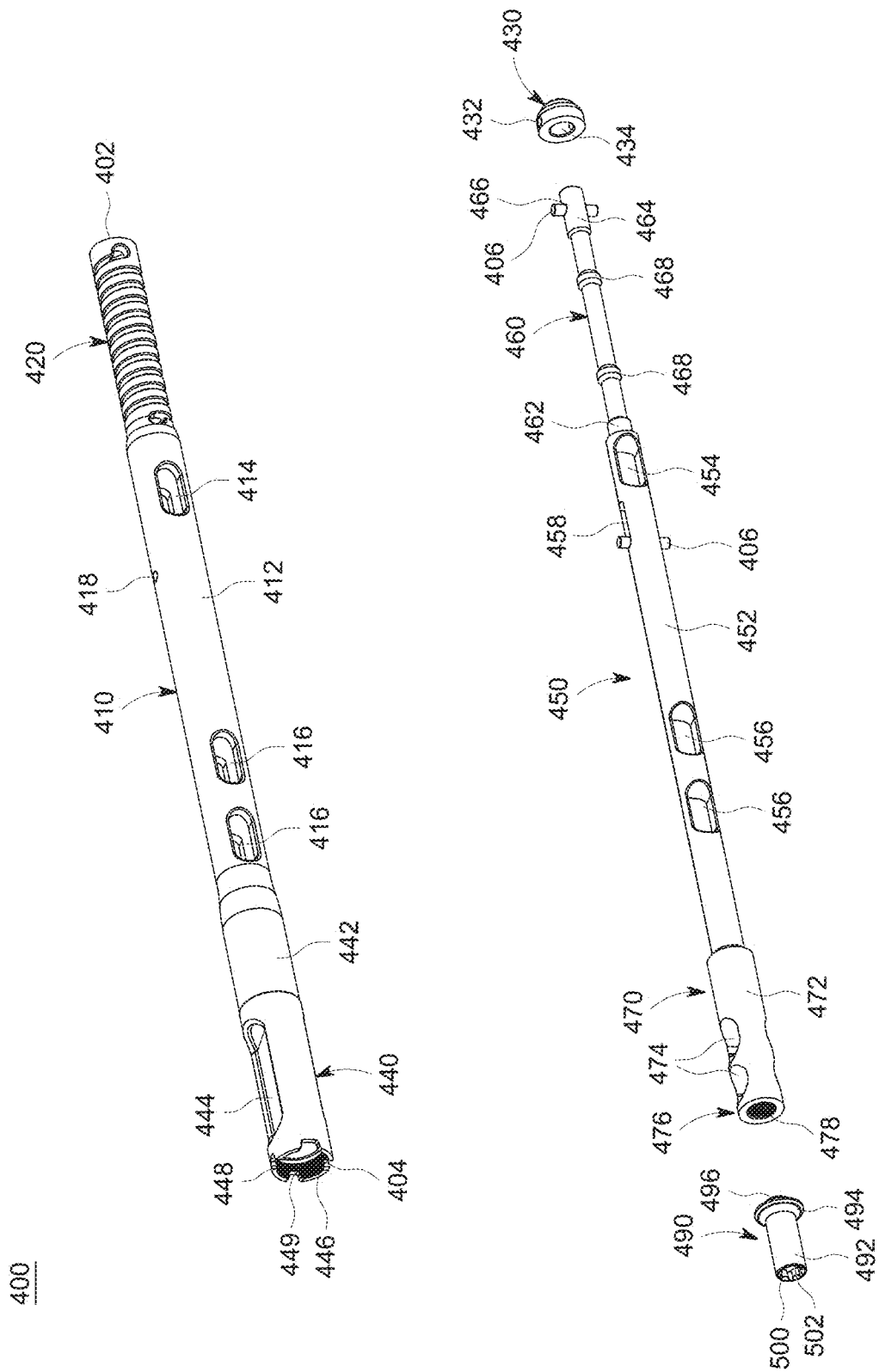
FIG. 44 is an exploded, second perspective view of the dynamic nail of FIG. 31, in accordance with an aspect of the present disclosure.

The distal end portion 440 of the first member 410 includes a shaft or body 442 coupled to the second end of the body portion 412. The distal end portion 440 may also include a distal or second through hole or fastener hole 444 positioned near the second end 404 of the implant 400. The second through hole 444 may be, for example, elongated or oval holes. The through hole 444 may extend through the body 442 from one side to the other side perpendicular to the longitudinal axis of the first member 410. As shown in FIG. 44, the distal end portion 440 may also include a threaded portion 446 positioned on an interior surface of the through hole 422 of the first member 410. The distal end portion 440 may also include at least one protrusion or tooth 448 positioned at the second end of the first member 410.

With continued reference to FIGS. 33, 34, 43 and 44, the second member or inner rod 450 includes a body portion or shaft 452 with an inner rod clip 460 coupled to and extending away from a first end of the second member 450 and a distal end portion 470 coupled to and extending away from a second end of the second member 450. The second member 450 may also include a first or proximal through hole or fastener hole 454 for receiving a bone screw or bone fastener. The through hole 454 may be positioned, for example, near the inner rod clip 460. The through hole 454 may be positioned to align with the through hole 414 of the first member 410 when assembled. The second member 450 may further include at least one second through hole or fastener hole 456 positioned near the distal end portion 470. The at least one second through hole 456 may be, for example, two through holes 456, as shown in the depicted embodiment. The second through holes 456 may be positioned to align with the second through holes 416 of the first member 410 when assembled. The second member 450 may also include at least one anti-rotation pin opening 458 configured or sized and shaped to receive an anti-rotation pin 406. The pin opening 458 may extend, for example, through the body 452 in a first direction while the holes 454, 456 extend through the body 452 in a second direction with the first direction being generally perpendicular to the second direction. The pin opening 458 may be, for example, positioned to align with the pin opening 418 to allow the pin 406 to be inserted through the pin opening 418 and pin opening 458 to secure the first member 410 to the second member 430.

Figure 33:
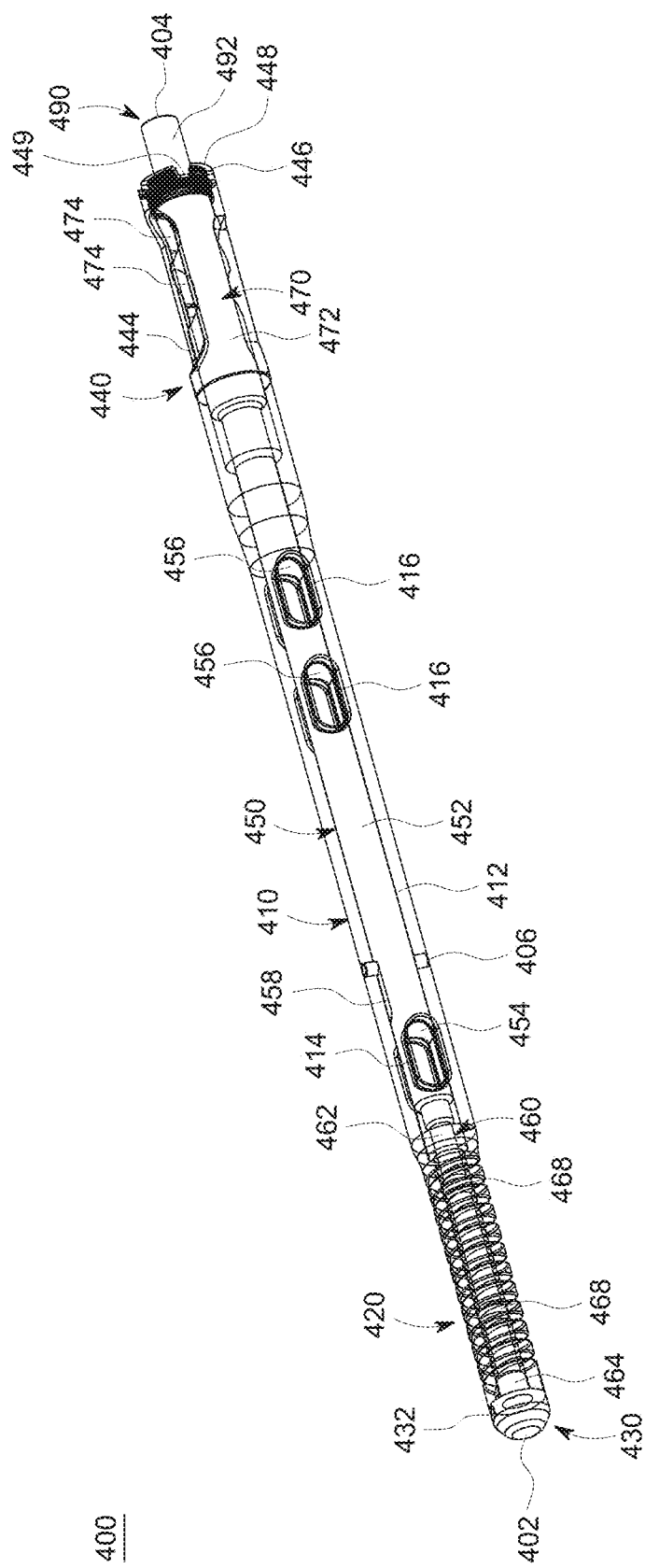
FIG. 33 is a third perspective view of the dynamic nail of FIG. 31 with a transparent body portion, in accordance with an aspect of the present disclosure.
Figure 34:
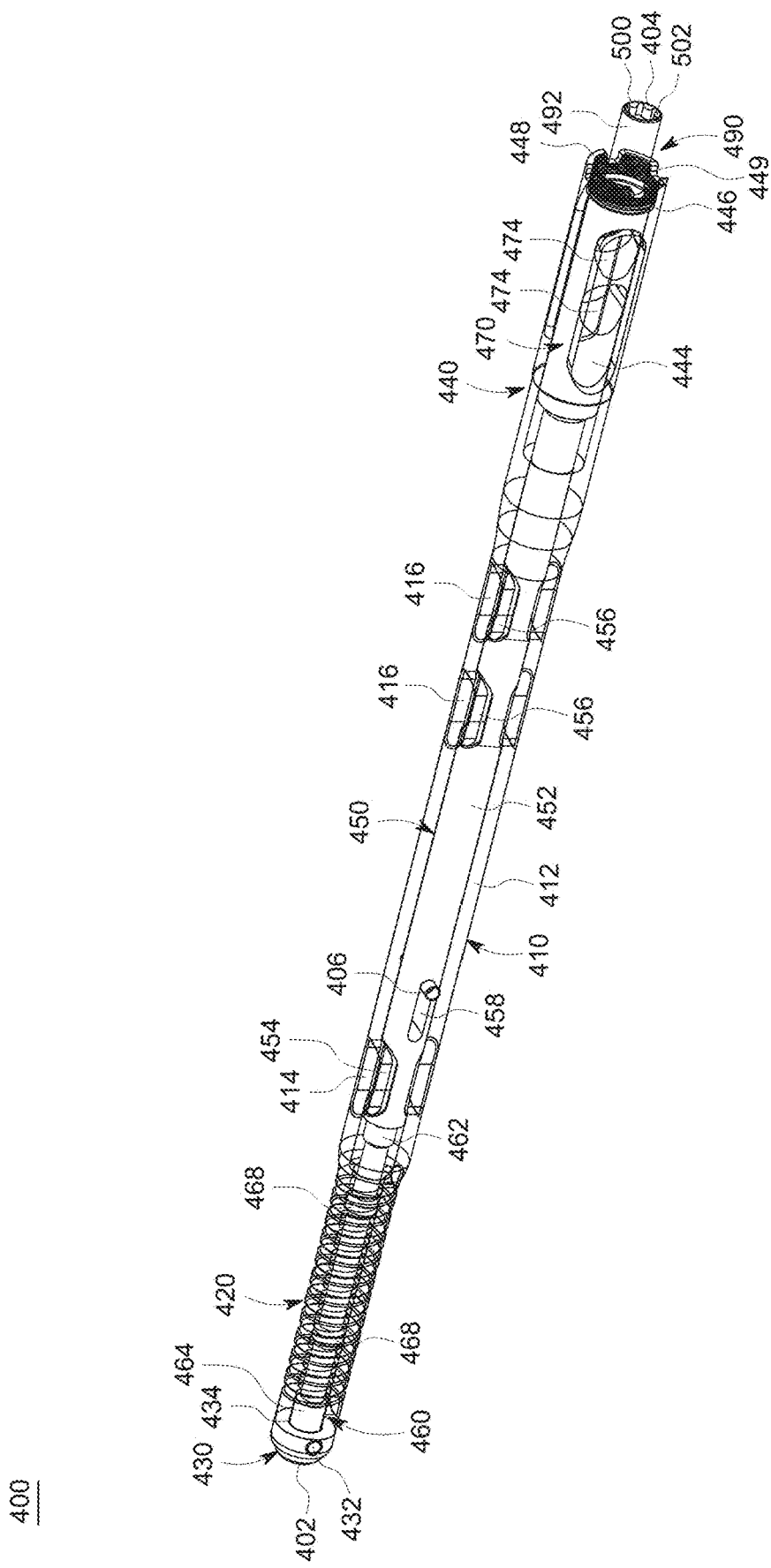
FIG. 34 is a fourth perspective view of the dynamic nail of FIG. 33, in accordance with an aspect of the present disclosure.
Figure 35:
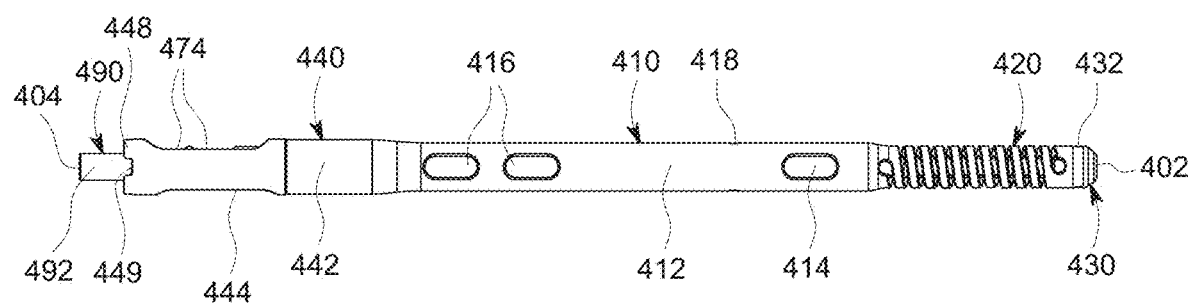
FIG. 35 is a first side view of the dynamic nail of FIG. 31, in accordance with an aspect of the present disclosure.
Figure 36:
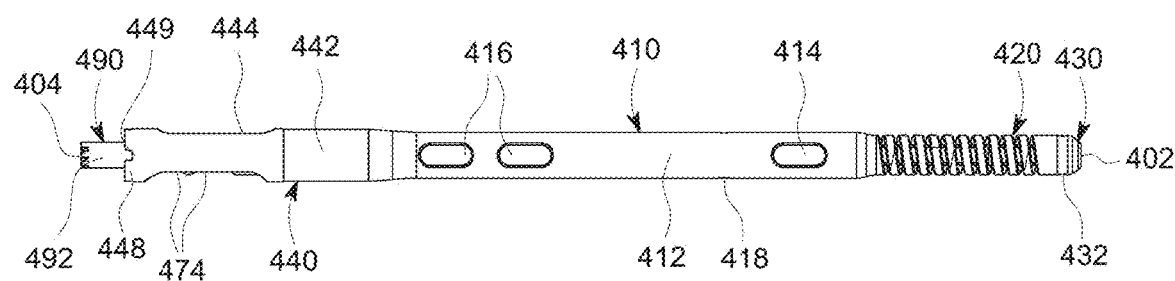
FIG. 36 is a second side view of the dynamic nail of FIG. 31, in accordance with an aspect of the present disclosure.
Figure 37:
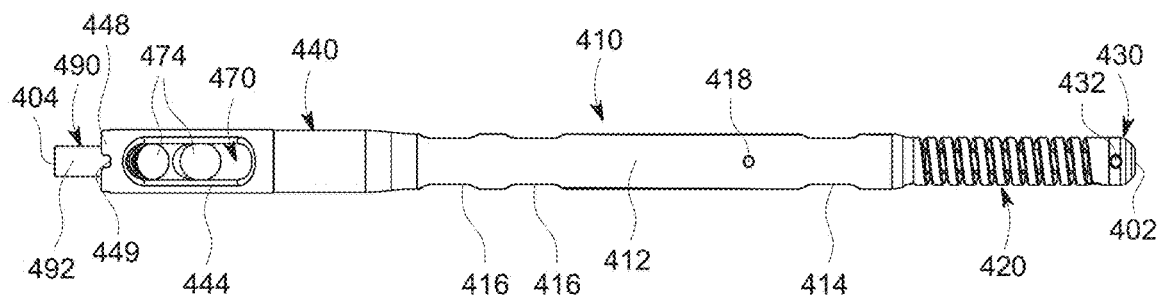
FIG. 37 is a third side view of the dynamic nail of FIG. 31, in accordance with an aspect of the present disclosure.
Figure 38:
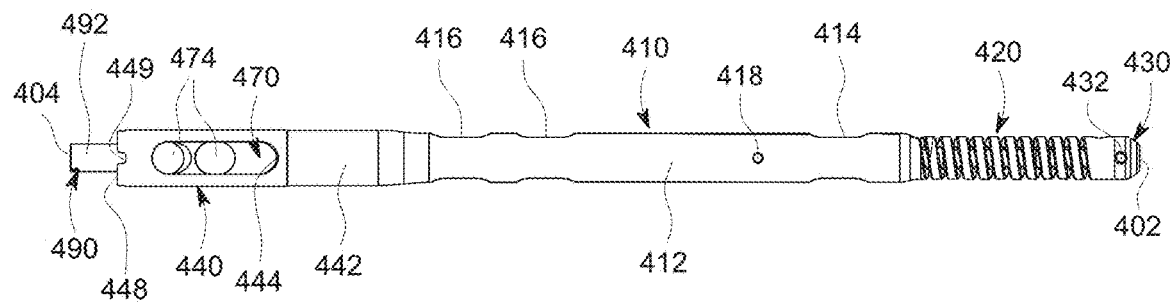
FIG. 38 is a fourth side view of the dynamic nail of FIG. 31, in accordance with an aspect of the present disclosure.
Figure 39:
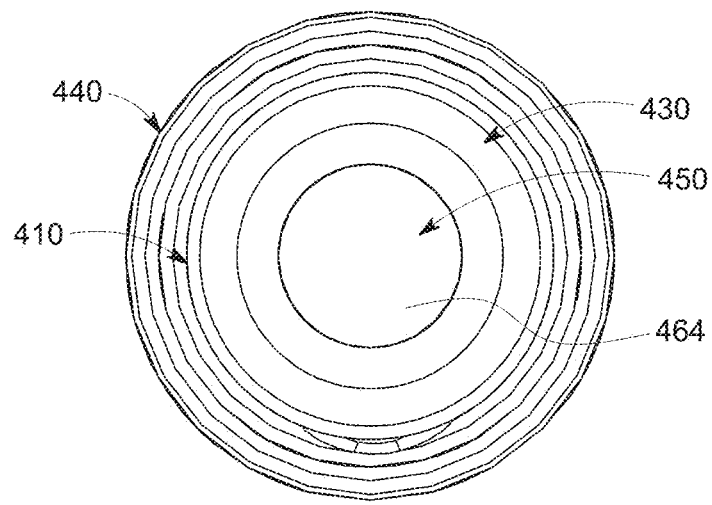
FIG. 39 is a first end view of the dynamic nail of FIG. 31, in accordance with an aspect of the present disclosure.
Figure 40:
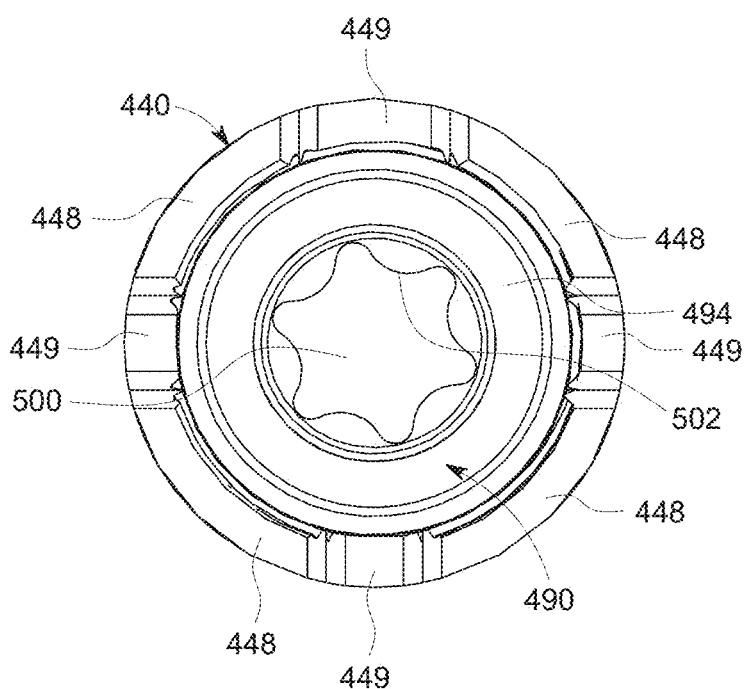
FIG. 40 is a second end view of the dynamic nail of FIG. 31, in accordance with an aspect of the present disclosure.
Figure 41:
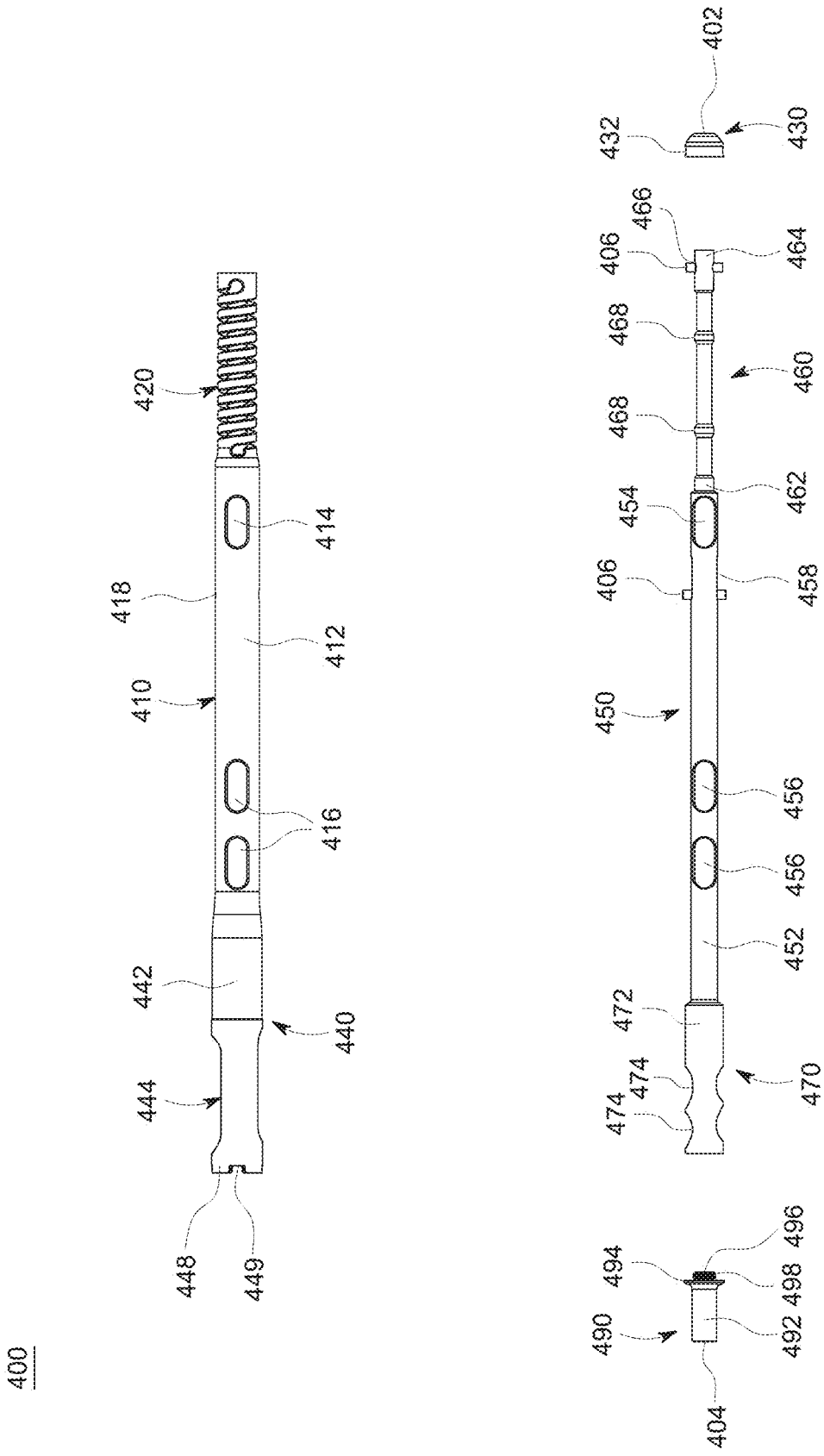
FIG. 41 is an exploded, first side view of the dynamic nail of FIG. 31, in accordance with an aspect of the present disclosure.
Figure 42:
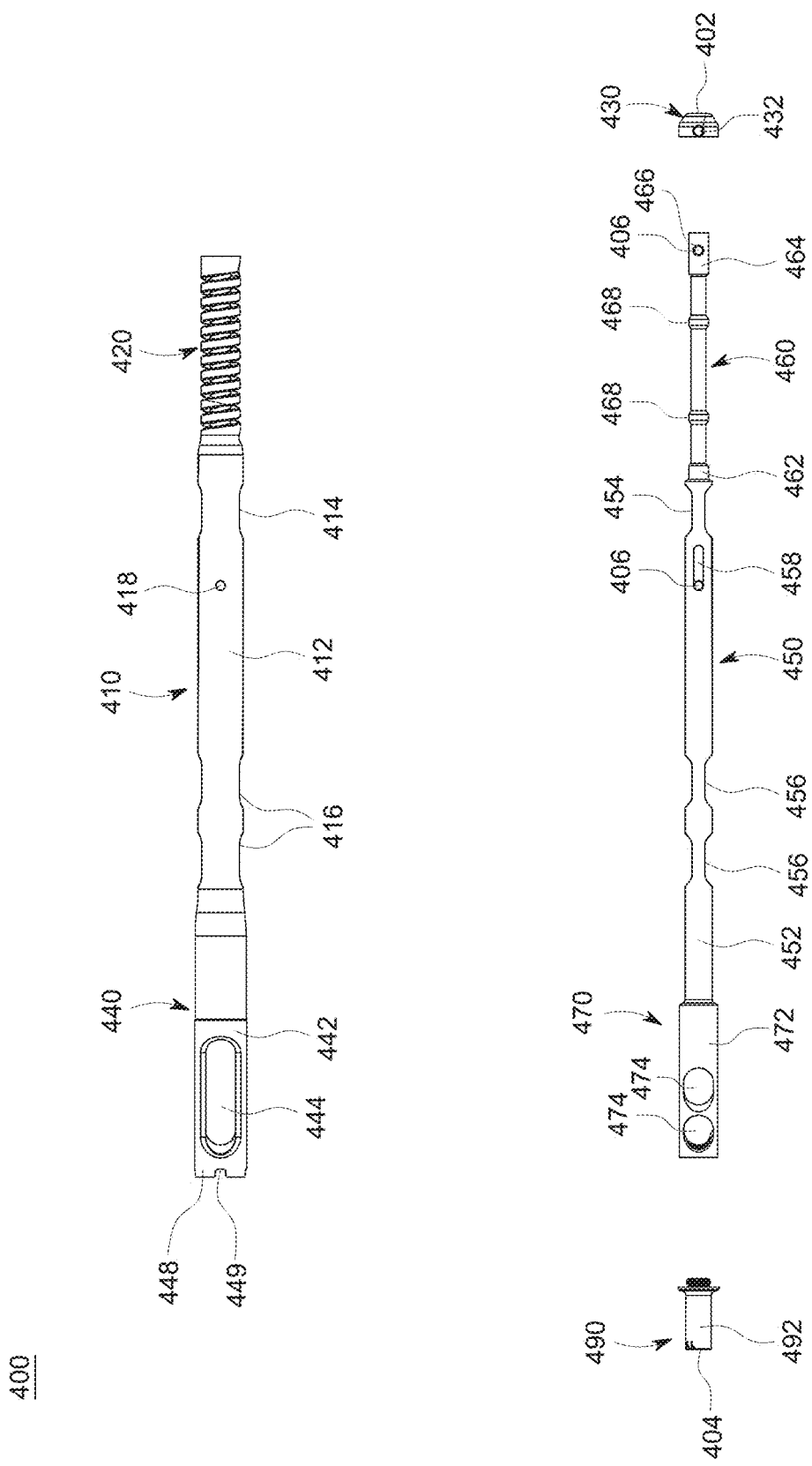
FIG. 42 is an exploded, second side view of the dynamic nail of FIG. 31, in accordance with an aspect of the present disclosure.
Figure 43:
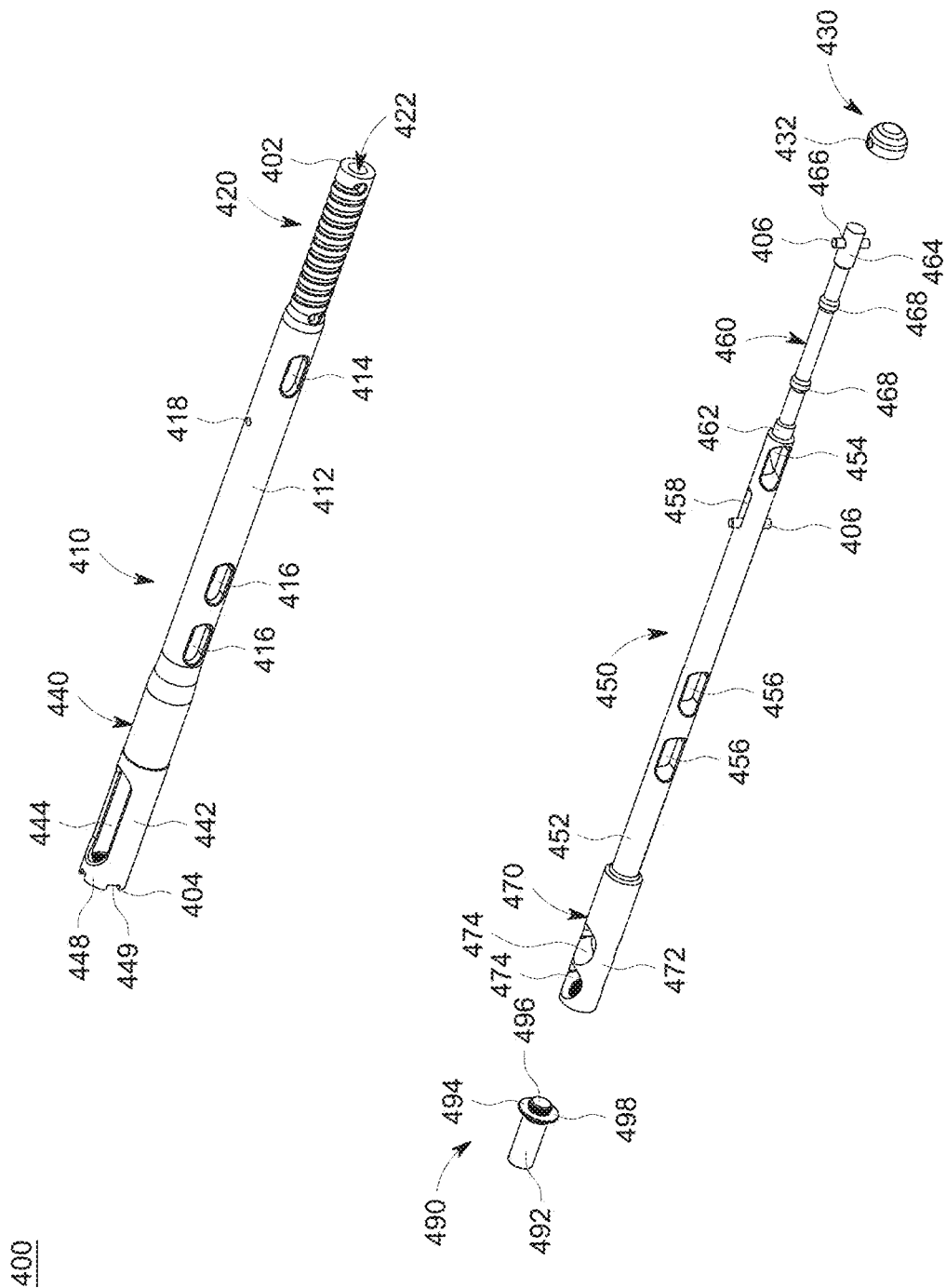
FIG. 43 is an exploded, first perspective view of the dynamic nail of FIG. 31, in accordance with an aspect of the present disclosure.

As shown in FIGS. 33, 34, 43 and 44, the inner rod clip 460 includes a stop portion 462 coupled directly to the body portion 452 at a first end of the inner rod clip 460. The inner rod clip 460 may have, for example, a first diameter and the stop portion 462 may have, for example, a second diameter that is larger than the first diameter. The second diameter of the stop portion 462 may also be, for example, smaller than the diameter of the body 452. The inner rod clip 460 may also include a coupling portion 464 positioned at a second end of the inner rod clip 460. The coupling portion 464 may have, for example, a third diameter that is larger than the first diameter of the inner rod clip 460. The coupling portion 464 may also include an anti-rotation pin opening 466 extending through the coupling portion 464 and is configured or sized and shaped to receive a pin 406. The inner rod clip 460 may also include at least one protrusion 468 extending circumferentially away from the inner rod clip 460. As shown, the at least one protrusion 468 may be, for example, two protrusions spaced along the longitudinal axis of the inner rod clip 460. The at least one protrusion 468 may be, for example, configured or sized and shaped to have an exterior diameter approximately the same size as the interior diameter of the deformable member 420. When assembled, the base portion 462 is positioned within the through hole 422 and surrounded by the deformable member 420, as shown in FIGS. 33 and 34. In an alternative embodiment, the inner rod clip 460 may include a slot (not shown) machined into it to allow for flexible tines (not shown). Once the tines of the inner rod clip 460 engage the outer sheath 410, the tines can help to prevent dissociation. The tines also transfer and hold the forces of the external spring 420.

The distal end portion 470 includes a shaft or body 472 extending away from the body portion 452 at an end opposite the inner rod clip 460. The distal end portion 470 also includes at least one second or distal through hole or fastener hole 474 for receiving a bone screw or bone fastener. As shown, the at least one second through hole 474 may be two second through holes 474. The distal end portion 470 further includes a coupling portion 476. The coupling portion 476 includes an opening 478 extending into the distal end portion 470 from the second end. The opening 478 may include internal threads along at least a portion of the opening 478.

With continued reference to FIGS. 33, 34, 43 and 44, the tension screw 490 may include a body portion 492 with a circumferential flange or protrusion 494 positioned near the second end of the body portion 492. The tension screw 490 may also include a coupling protrusion 496 coupled to and/or extending away from the second end of the body portion 492. The coupling protrusion 496 may also extend away from the flange 494 to the second end of the tension screw 490. The coupling protrusion 496 may include, for example, an exterior threaded portion 498 for engaging the internal threads of the through hole 478 to place the implant 400 into tension. The tension screw 490 may also include a recessed region 500 extending into the first end of the body portion 492. The recessed region 500 may include, for example, a drive opening or tool engagement opening 502 for receiving an insertion, removal or adjustment tool. The tool engagement opening 502 may receive a tool to remove the pre-loaded compression from the implant 400. The tension screw 490 holds the proximal external spring 420 in compression. Thus, the implant 400 may be ready for insertion into a patient in a "pre-loaded" position, which includes compression of the deformable member 420 and positioning the anti-rotation pins 406 at the bottom of their respective slots. More specifically, the tension screw 490 may be, for example, releasably couplable with the implant 400 such that manipulation and/or release of the tension screw 490 actuates the proximal external spring 420 from a pre-loaded (e.g., compressed) position to a loaded (e.g., at least partially compressed) position.

The IM nails 100, 300, 400 provide, for example, continuous compression across both the tibio-talar or ankle joint and the talo-calcaneal or subtalar joint. The IM nails 100, 300, 400 provide continuous compression at the joints to ensure that bony apposition is maintained throughout the healing process. In an embodiment, the IM nails 300 allow for different compressive loads at each joint. The internal spring 350 and external spring 120 provide compression to the two joints independently, thereby providing the optimum compression at each joint to promote bone healing and prevent joint gaping. The IM nail 300 provides continual compression in the tibio-talo-calcaneal joints of the ankle, between the talus and tibia, as well as talus and calcaneus. The compression is dynamized to allow for continual compression on the joint surfaces as bone resorption, or remodeling, occurs.

A method of using the implant 100, 300, 400, as shown in FIGS. 29 and 30. The method may be performed to aid in TTC fusions of the ankle complex. The method may include obtaining a pre-compressed implant 100, 300, 400. The implant 100, 300, 400 may be inserted in a pre-loaded compressed position. For example, the method may include inserting the implant 100, 300, 400 into the patient with the spring 120, 420 in the compressed position. The method further includes inserting crossing screws or fasteners 308 through the patient's bones and the implant 100, 300, 400. The implant 100, 300, 400 may remain in the compressed position while the fasteners 308 are inserted. After the fasteners 308 are inserted, the disposable tension screw is released or removed to activate the compression and the implant 100, 300, 400 moves to a second loaded position that may be, for example, at least partially compressed. For example, the tension screw 190, 490 may be, for example, releasably couplable with the implant 100, 300, 400 such that manipulation and/or release of the tension screw 190, 490 actuates the proximal external spring 120 from a pre-loaded (e.g., compressed) position to a loaded (e.g., at least partially compressed) position. Finally, the surgical incision is closed.

Figure 45:
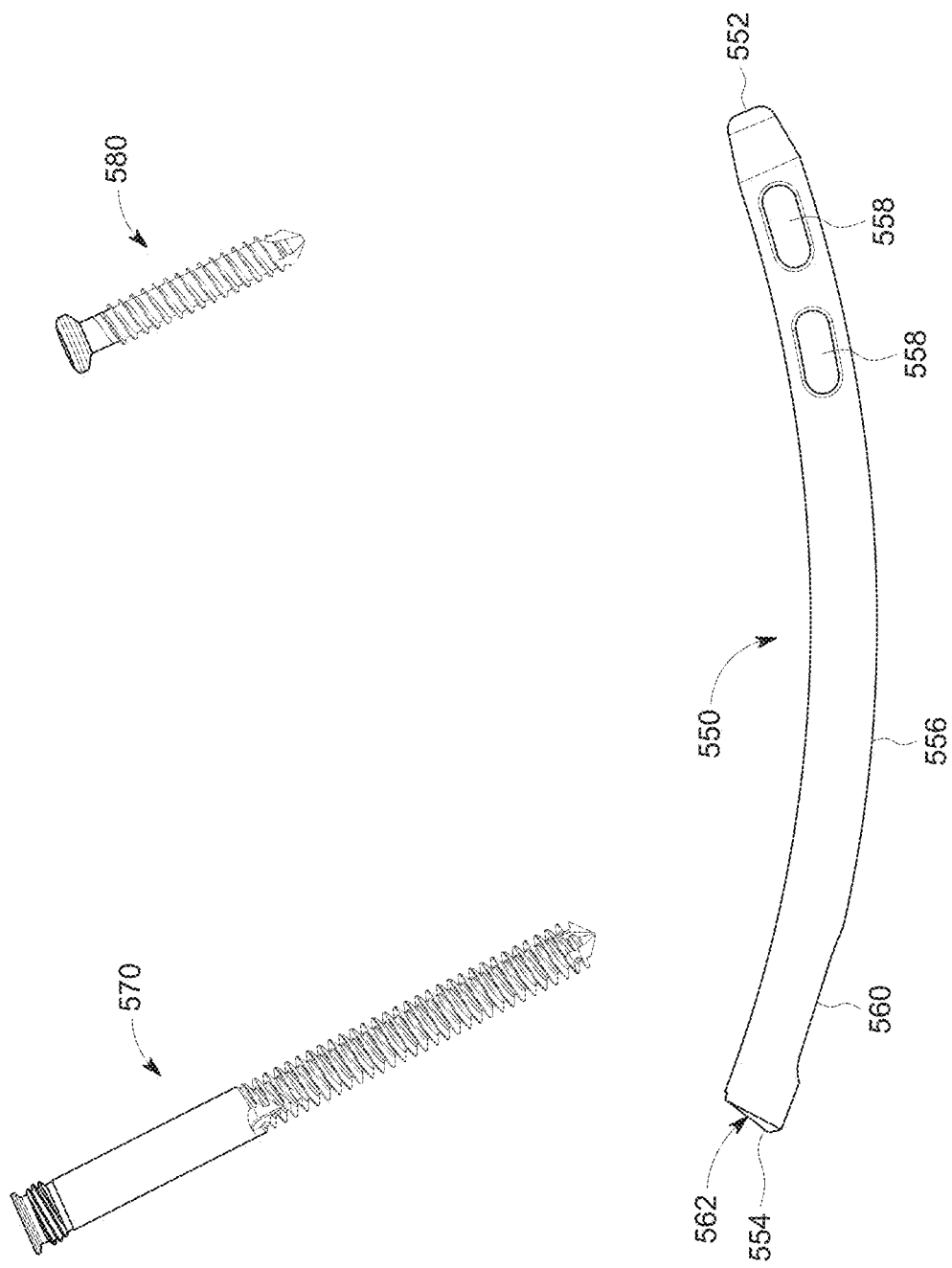
FIG. 45 is an exploded, side view of a curved nail system, in accordance with an aspect of the present disclosure.
Figure 46:
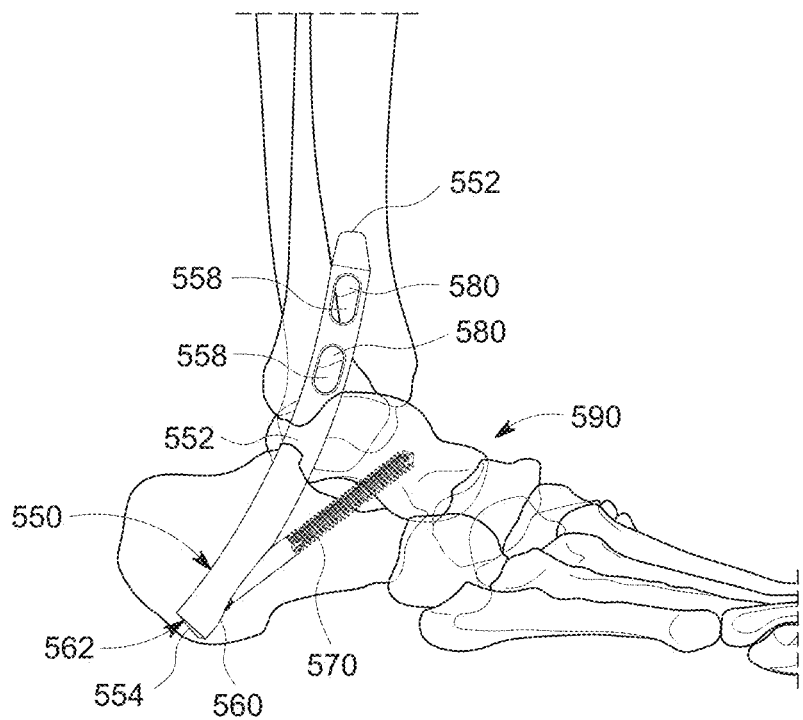
FIG. 46 is a side view of the curved nail system of FIG. 45 implanted into a patient's lower extremity, in accordance with an aspect of the present disclosure.

Referring now to FIGS. 45-46, a dynamic nail system or curved nail system is shown. The nail system includes a curved nail or curved implant 550, a first fastener 570, and at least one second fastener. The curved nail 550 may have a first end 552 and a second end 554. The nail 550 may include a shaft or body portion 556 extending between the first end 552 and the second end 554. The curved nail 550 may also include at least one proximal or first through hole 558 positioned near the first end 552. Further, the curved nail 550 may include at least one distal or second through hole 560 positioned near the second end. The second through hole 560 may be, for example, an elongated or oval hole 560 extending through the nail 550 at an angle. The first through holes 558 may extend through the nail 550 in a first direction and the second through hole 560 may extend through the nail 550 in a second direction. The first direction of through hole 560 may be positioned, for example, rotated circumferentially with respect to or offset from the second direction of the second through holes 558.

Figure 47:
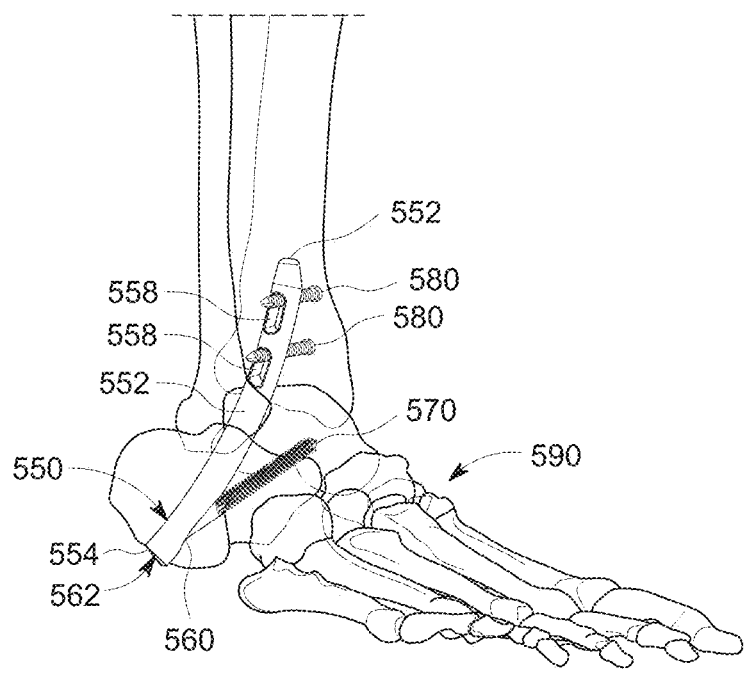
FIG. 47 is a perspective view of the curved nail system and lower extremity of FIG. 46, in accordance with an aspect of the present disclosure.

Referring now to FIGS. 46-47, the implant 550 inserted into a patient's ankle 590 is shown. The nail 550 may be inserted as shown in FIGS. 46 and 47 in a compressed state. Next, the fasteners 570, 580 may be inserted into the patient's lower extremity 590 and through the nail 550. Specifically, the first fastener 570 may be inserted through the distal through hole 560 and across the patient's joint. The second fasteners 580 may be inserted through the at least one proximal through hole 558 and across the patient's joint.

As may be recognized by those of ordinary skill in the art based on the teachings herein, numerous changes and modifications may be made to the above-described and other embodiments of the present disclosure without departing from the scope of the disclosure. The components of the instruments, guides, implants, plates, and/or systems as disclosed in the specification, including the accompanying abstract and drawings, may be replaced by alternative component(s) or feature(s), such as those disclosed in another embodiment, which serve the same, equivalent or similar purpose as known by those skilled in the art to achieve the same, equivalent or similar results by such alternative component(s) or feature(s) to provide a similar function for the intended purpose. In addition, the instruments, guides, implants, plates, and/or systems may include more or fewer components or features than the embodiments as described and illustrated herein. For example, the components and features of FIGS. 1-14, FIGS. 15-30, FIGS. 31-44 and FIGS. 45-47 may be used interchangeably and in alternative combinations as would be modified or altered by one of skill in the art. Further, the steps of the surgical methods associated with the systems of FIGS. 1-14, FIGS. 15-30, FIGS. 31-44 and FIGS. 45-47 may be used interchangeably and in alternative combinations as would be modified or altered by one of skill in the art. Accordingly, this detailed description of the currently-preferred embodiments is to be taken in an illustrative, as opposed to limiting of the disclosure.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has", and "having"), "include" (and any form of include, such as "includes" and "including"), and "contain" (and any form of contain, such as "contains" and "containing") are open-ended linking verbs. As a result, a method or device that "comprises," "has," "includes," or "contains" one or more steps or elements possesses those one or more steps or elements, but is not limited to possessing only those one or more steps or elements. Likewise, a step of a method or an element of a device that "comprises," "has," "includes," or "contains" one or more features possesses those one or more features, but is not limited to possessing only those one or more features. Furthermore, a device or structure that is configured in a certain way is configured in at least that way, but may also be configured in ways that are not listed.

The invention has been described with reference to the preferred embodiments. It will be understood that the operational embodiments described herein are exemplary of a plurality of possible arrangements to provide the same general features, characteristics, and general system operation. Modifications and alterations will occur to others upon a reading and understanding of the preceding detailed description. It is intended that the invention be construed as including all such modifications and alterations.

Having thus described the preferred embodiment, the invention is now claimed to be:

1. A nail system, comprising:
a first member with a first deformable member positioned at a first end of the first member; and
a second member received within the first member, wherein the second member comprises:
a body portion with a first end and a second end;
an inner rod clip coupled to the first end of the body portion of the second member, wherein a portion of the inner rod clip extends beyond the first end of the first member, wherein the extending portion of the inner rod clip includes an anti-rotation pin opening, and wherein the anti-rotation pin opening of the inner rod clip receives a first pin; and
a distal end portion coupled to the second end of the body portion of the second member.

2. The nail system of claim 1, wherein the first member comprises:
a body portion with the first deformable member coupled to the first end; and
a distal end portion coupled to a second end of the body portion.

3. The nail system of claim 2, wherein the body portion of the first member comprises:
a first through hole extending through the body portion; and
at least one second through hole extending through the body portion;
wherein the at least one second through hole is positioned along a longitudinal axis between the first through hole and the second end.

4. The nail system of claim 3, wherein the body portion of the first member further comprises:
an anti-rotation pin opening extending through the body portion of the first member, wherein an anti-rotation pin is positioned between the first through hole of the first member and the at least one second through hole of the first member.

5. The nail system of claim 4, wherein the anti-rotation pin opening of the first member is circumferentially offset from the first through hole of the first member and the at least one second through hole of the first member.

6. The nail system of claim 4, wherein the first member further comprises:
a third through hole extending through the first member from the first end to the second end.

7. The nail system of claim 4, wherein the distal end portion of the first member comprises:
a body portion; and
a distal through hole extending through the body portion, wherein the distal through hole is an elongated hole.

8. The nail system of claim 7, wherein the distal end portion of the first member further comprises:
a threaded portion positioned within a third through hole extending through the first member from the first end to the second end of the first member;
at least one protrusion extending away from the second end of the body portion of the first member; and
at least one recess extending into the body portion of the first member and positioned between at least two protrusions of the at least one protrusion.

9. The nail system of claim 7, wherein the distal through hole of the first member extends through the body portion perpendicular to the first through hole of the first member and the at least one second through hole of the first member.

10. The nail system of claim 1, wherein the body portion of the second member further comprises:
a first through hole positioned near the second end of the body portion of the second member;
at least one second through hole positioned near the first end of the body portion of the second member; and
an anti-rotation pin opening positioned between the first through hole of the second member and the at least one second through hole of the second member.

11. The nail system of claim 10, wherein the anti-rotation pin opening of the second member is circumferentially offset from the first through hole of the second member and the at least one second through hole of the second member.

12. The nail system of claim 10, wherein the inner rod clip comprises:
a stop portion at a first end;
a coupling portion at a second end; and
at least one protrusion extending away from the inner rod clip, wherein the at least one protrusion is positioned along a length of the inner rod clip between the stop portion and the coupling portion.

13. The nail system of claim 12, wherein the distal end portion of the second member comprises:
a body with a first end and a second end;
at least one distal through hole extending through the body of the distal end portion of the second member; and
a coupling portion positioned at the first end of the body of the distal end portion of the second member, wherein the coupling portion of the distal end portion includes internal threads.

14. The nail system of claim 13, further comprising:
a coupling member positioned to secure the first member to the second member at a first end of the nail system.

15. The nail system of claim 14, wherein the coupling member comprises:
an anti-rotation pin opening; and
a through hole extending through the coupling member along a longitudinal axis of the coupling member, wherein the anti-rotation pin opening of the coupling member extends perpendicular to the through hole.

16. The nail system of claim 15, wherein the anti-rotation pin opening of the coupling member aligns with the anti-rotation pin opening of the inner rod clip of the second member to receive the first pin.

17. The nail system of claim 15, further comprising:
a tension screw coupled to the second end of the second member to secure the first member to the second member.

18. The nail system of claim 17, wherein the tension screw comprises:
a body portion;
a flange extending away from the body portion of the tension screw near a first end; and
a coupling protrusion extending away from the first end of the body portion of the tension screw.

19. The nail system of claim 18, wherein an exterior surface of the coupling protrusion of the tension screw is threaded.

20. The nail system of claim 18, wherein the tension screw further comprises:
a recessed region extending into a second end of the body portion of the tension screw; and
a drive opening positioned within the recessed region.

21. The nail system of claim 20, wherein the second member is inserted in the through hole of the first member, wherein a first through hole of the first member aligns with the first through hole of the second member, and at least one second through hole of the first member aligns with the at least one second through hole of the second member.

22. The nail system of claim 21, wherein the at least one distal through hole of the distal end portion of the second member aligns with a distal through hole of the first member.

23. The nail system of claim 1, wherein the second member comprises:
  a second deformable member positioned at a second end of the second member.

24. The nail system of claim 23, wherein the second deformable member is a spring.

25. The nail system of claim 1, wherein the first deformable member is a spring.

* * * * *